United States Patent
Everley et al.

(10) Patent No.: US 11,085,927 B2
(45) Date of Patent: Aug. 10, 2021

(54) TECHNIQUES FOR HIGH THROUGHPUT TARGETED PROTEOMIC ANALYSIS AND RELATED SYSTEMS AND METHODS

(71) Applicant: President and Fellows of Harvard College, Cambridge, MA (US)

(72) Inventors: Robert A. Everley, Niantic, CT (US); Brian K. Erickson, Brookline, MA (US); Christopher Michael Rose, Fremont, CA (US); Steven P. Gygi, Foxborough, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 95 days.

(21) Appl. No.: 16/306,686

(22) PCT Filed: Jun. 1, 2017

(86) PCT No.: PCT/US2017/035446
§ 371 (c)(1),
(2) Date: Dec. 3, 2018

(87) PCT Pub. No.: WO2017/210427
PCT Pub. Date: Dec. 7, 2017

(65) Prior Publication Data
US 2019/0310264 A1    Oct. 10, 2019

Related U.S. Application Data

(60) Provisional application No. 62/345,532, filed on Jun. 3, 2016.

(51) Int. Cl.
*G01N 33/68* (2006.01)
*H01J 43/26* (2006.01)
*G01N 33/50* (2006.01)

(52) U.S. Cl.
CPC .......... *G01N 33/6848* (2013.01); *H01J 43/26* (2013.01); *G01N 2458/15* (2013.01)

(58) Field of Classification Search
CPC .......... G01N 33/6848; G01N 33/6803; G01N 33/68; G01N 33/50; G01N 2458/15; G01N 2458/00; H01J 43/26
(Continued)

(56) References Cited

U.S. PATENT DOCUMENTS

| | | | |
|---|---|---|---|
| 4,849,628 A | 7/1989 | McLuckey et al. | |
| 5,696,376 A | 12/1997 | Doroshenko et al. | |

(Continued)

FOREIGN PATENT DOCUMENTS

| | | |
|---|---|---|
| EP | 1385194 A2 | 1/2004 |
| GB | 2462190 A | 2/2010 |

(Continued)

OTHER PUBLICATIONS

Office Action for U.S. Appl. No. 13/901,137 dated Aug. 20, 2015.
(Continued)

*Primary Examiner* — Christine T Mui
(74) *Attorney, Agent, or Firm* — Wolf, Greenfield & Sacks, P.C.

(57) ABSTRACT

Described herein is a kit of materials prepared for assays that involve determining relative abundance and/or absolute abundance of various targeted peptides. The kit may comprise trigger versions of target peptides with masses offset from the respective target peptides by predetermined and known amounts. The trigger peptides may be present in amounts that may be readily detected via a mass spectrometry analysis. When mixed with samples that are analyzed, detection of the trigger peptides indicates where in the mass-spectrometer output the target peptide may be found. The kit may include a predetermined amount of synthetic (Continued)

versions of one or more of the target peptides. A measured relative abundance of this synthetic peptide relative to that of the target peptides yields an absolute quantitative value of the target peptide. Also disclosed is a method of preparing a plurality of samples to be submitted for mass spectrometer analysis in parallel.

18 Claims, 11 Drawing Sheets

(58) Field of Classification Search
USPC .............................................. 436/15; 422/430
See application file for complete search history.

(56) References Cited

U.S. PATENT DOCUMENTS

| 7,569,814 | B2 | 8/2009 | Hashimoto et al. |
| 7,919,745 | B2 | 4/2011 | Shilov et al. |
| 9,437,407 | B2 | 9/2016 | McAlister et al. |
| 10,145,818 | B2 | 12/2018 | Wuhr et al. |
| 2002/0192708 | A1 | 12/2002 | Steen et al. |
| 2004/0072251 | A1 | 4/2004 | Anderson |
| 2004/0229283 | A1* | 11/2004 | Gygi ................ G01N 33/68 435/7.1 |
| 2005/0124014 | A1* | 6/2005 | Chen ............... G01N 33/6803 435/7.32 |
| 2005/0242278 | A1 | 11/2005 | Syage et al. |
| 2007/0084994 | A1 | 4/2007 | Wang et al. |
| 2008/0044857 | A1 | 2/2008 | Anderson |
| 2008/0142705 | A1 | 6/2008 | Schwartz et al. |
| 2008/0230691 | A1 | 9/2008 | Hager |
| 2009/0194688 | A1 | 8/2009 | Bateman et al. |
| 2009/0283673 | A1 | 11/2009 | Shilov et al. |
| 2010/0084547 | A1 | 4/2010 | Pringle et al. |
| 2010/0311176 | A1 | 12/2010 | Williamson et al. |
| 2011/0006200 | A1 | 1/2011 | Loboda |
| 2011/0111513 | A1 | 5/2011 | Baumann et al. |
| 2011/0297823 | A1 | 12/2011 | Coon et al. |
| 2011/0318771 | A1 | 12/2011 | Li |
| 2012/0044857 | A1 | 2/2012 | Kim et al. |
| 2012/0091330 | A1 | 4/2012 | Coon et al. |
| 2012/0178118 | A1 | 7/2012 | Pi et al. |
| 2012/0261568 | A1 | 10/2012 | Coon et al. |
| 2012/0305762 | A1 | 12/2012 | Kaneko et al. |
| 2013/0183704 | A1 | 7/2013 | Shin et al. |
| 2013/0334414 | A1 | 12/2013 | McAlister et al. |
| 2014/0364337 | A1 | 12/2014 | Hermanson et al. |
| 2015/0293058 | A1 | 10/2015 | Wuhr et al. |
| 2016/0020083 | A1 | 1/2016 | McAlister et al. |

FOREIGN PATENT DOCUMENTS

| JP | 2008-519410 | A | 6/2008 |
| JP | 2010-514103 | A | 4/2010 |
| JP | 2010-249838 | A | 11/2010 |
| JP | 2011-529260 | A | 12/2011 |
| JP | 2012-186180 | A | 9/2012 |
| WO | WO 01/86306 | A2 | 11/2001 |
| WO | WO 01/94935 | A2 | 12/2001 |
| WO | WO 02/052259 | A1 | 7/2002 |
| WO | WO 2006/084130 | A3 | 8/2006 |
| WO | WO 2006/086540 | A1 | 8/2006 |
| WO | WO 2007/087534 | A2 | 8/2007 |
| WO | WO 2008/142579 | A2 | 11/2008 |
| WO | WO 2010/109022 | A1 | 9/2010 |
| WO | WO 2012/026743 | A2 | 3/2012 |
| WO | WO 2012/051392 | A2 | 4/2012 |
| WO | WO 2012/164378 | A2 | 12/2012 |

OTHER PUBLICATIONS

International Search Report and Written Opinion for International Application No. PCT/US2013/040395 dated Sep. 13, 2013.
International Preliminary Report on Patentability for Application No. PCT/US2013/040395 dated Dec. 4, 2014.
Extended European Search Report for European Application No. EP 13848897.8 dated May 12, 2016.
European Communication for European Application No. 13848897.8 dated Sep. 13, 2018.
European Communication for European Application No. 13848897.8 dated Nov. 16, 2018.
International Search Report and Written Opinion for Application No. PCT/US2013/066010 dated Jan. 17, 2014.
International Preliminary Report on Patentability for Application No. PCT/US2013/066010 dated May 7, 2015.
International Search Report and Written Opinion for Application No. PCT/US2014/023851 dated Jul. 21, 2014.
International Preliminary Report on Patentability for Application No. PCT/US2014/023851 dated Sep. 24, 2015.
Invitation to Pay Additional Fees for Application No. PCT/US2014/041686 dated Sep. 25, 2014.
International Search Report and Written Opinion for Application No. PCT/US2014/041686 dated Jan. 9, 2015.
International Preliminary Report on Patentability for Application No. PCT/US2014/041686 dated Dec. 23, 2015.
International Search Report and Written Opinion for International Application No. PCT/US17/35446 dated Sep. 26, 2017.
International Preliminary Report on Patentability for International Application No. PCT/US2017/035446 dated Dec. 13, 2018.
Arnott et al., Selective Detection of Membrane Proteins Without Antibodies. Research. The American Society for Biochemistry and Molecular Biology, Inc. Molecular and Cellular Proteomics 1.2. 2002. 9 pages.
Borisov et al., Low-Energy Collision-Induced Dissociation Fragmentation Analysis of Cysteinyl-Modified Peptides. Anal. Chem. 2002;74:2284-92.
Byers et al., Candidate verification of iron-regulated Neisseria meningitidis proteins using isotpic versions of tandem mass tags (TMT) and single reaction monitoring. Journal of Proteomics 2009;73:231-9.
Costa et al., Model Fitting and Error Estimation. Systems Biology: Biomedical Modeling. 2010. 34 pages.
Dasari et al., Quantification of Isotopically Overlapping Deamidated and 18O-Labeled Peptides Using Isotopic Envelope Mixture Modelling. Journal of Proteome Research, 2009;8:1263-70.
Lu et al. Sulfonium Ion Derivatization, Isobaric Stable Isotope Labeling and Data Dependent CID- and ETD-MS/MS for Enhanced Phosphopeptide Quantitation, Identification and Phosphorylation Site Characterization. Focus: MS/MS Peptide Identification: Research Article. J. Am. Soc. Mass Spectrom. 2012;23:577-93.
Mertins et al., iTRAQ Labeling is Superior to mTRAQ for Quantitative Global Proteomics and Phosphoproteomics. Technological Innovation and Resources. 2012. 12 pages.
Savitski et al., Delayed fragmentation and optimized isolation width settings for improvement of protein identification and accuracy of isobaric mass tag quantification on Orbitrap-type mass spectrometers. Anal Chem. Dec. 2011; 83(23):8959-67. doi: 10.1021/ac201760x.
Second et al., Dual-pressure linear ion trap mass spectrometer improving the analysis of complex protein mixtures. Anal Chem. Sep. 2009; 81(18):7757-65. doi: 10.1021/ac901278y. PubMed PMID: 19689114.
Yan et al., Index-ion Triggered MS2 Ion Quantification: A Novel Proteomics Approach for Reproducible Detection and Quantification of Targeted Proteins in Complex Mixtures. Technological Innovation and Resources. 2011. 16 pages.

* cited by examiner

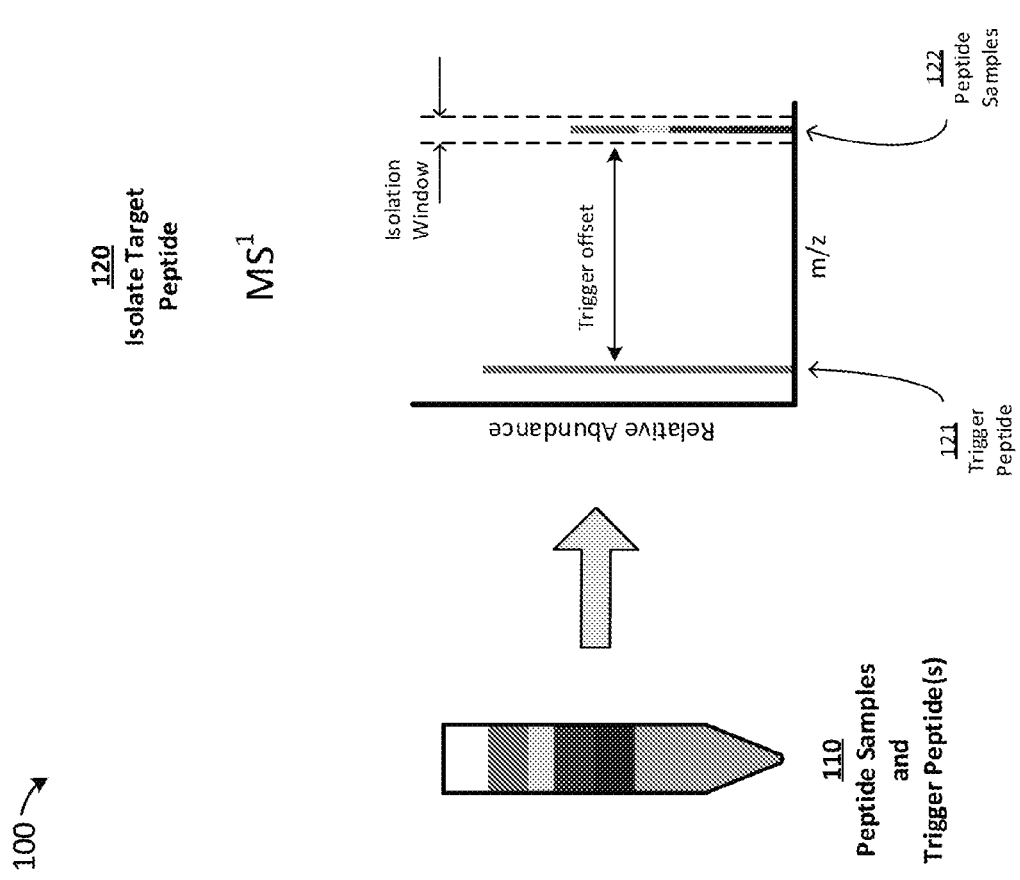
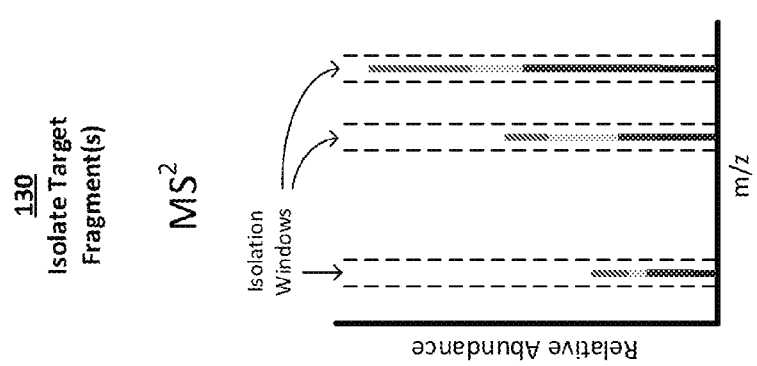
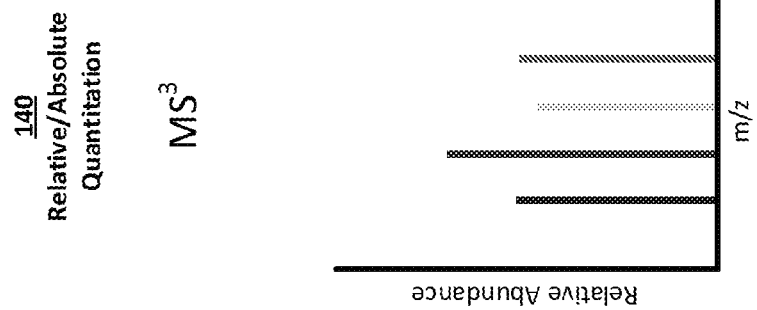
FIG. 1A
FIG. 1B
FIG. 1C

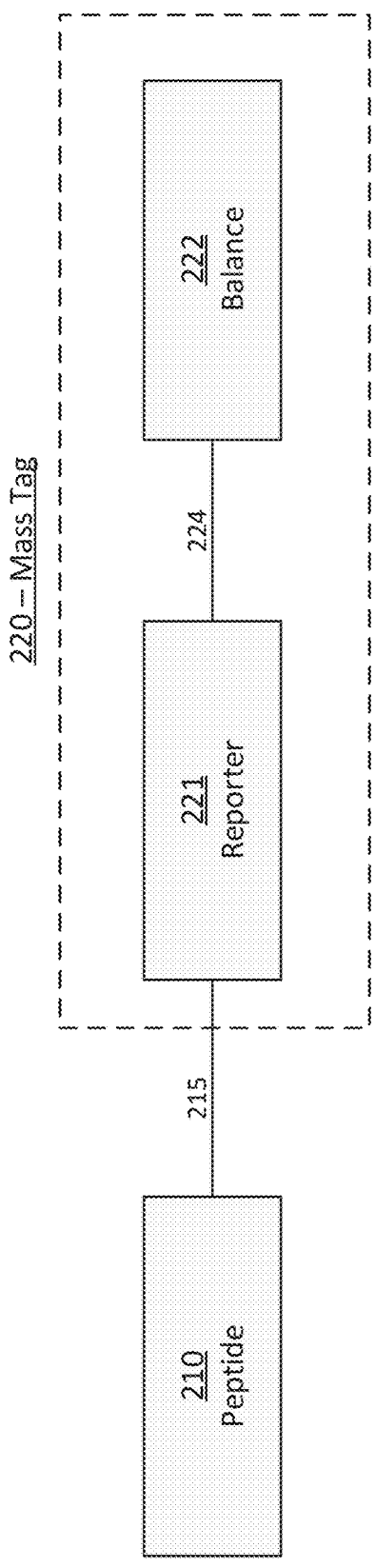

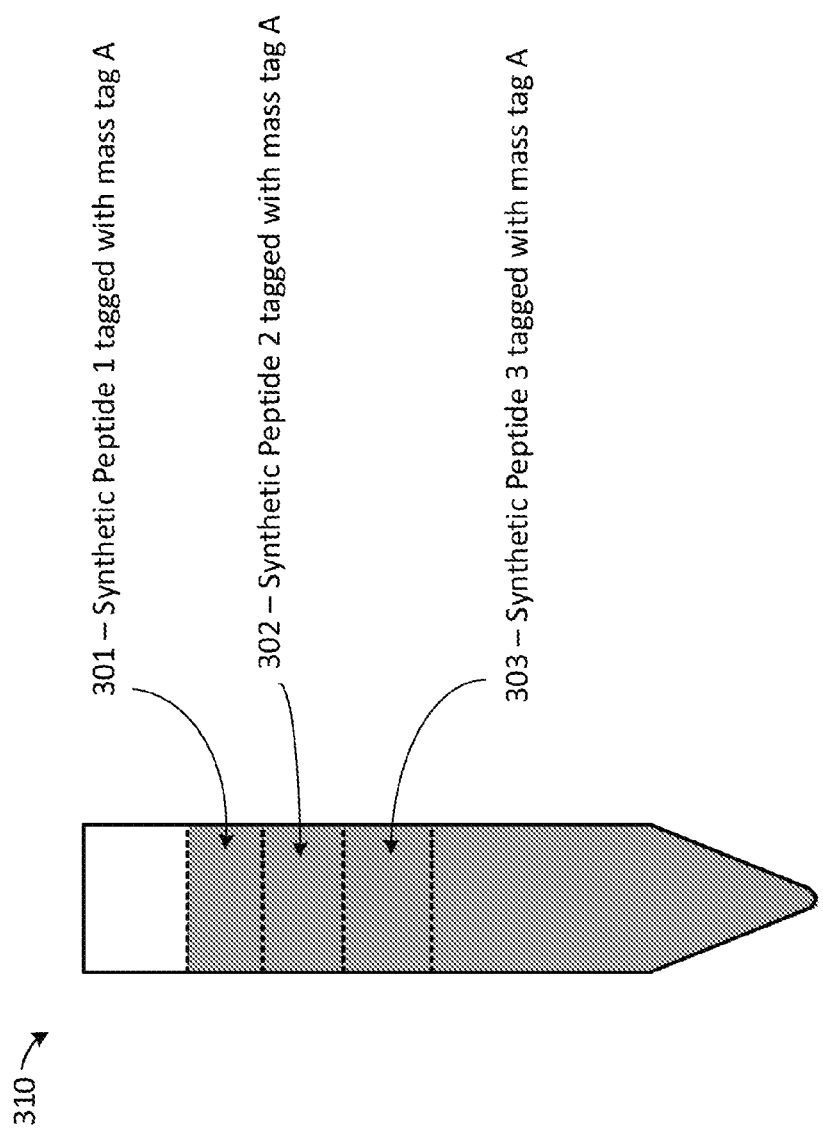

TECHNIQUES FOR HIGH THROUGHPUT TARGETED PROTEOMIC ANALYSIS AND RELATED SYSTEMS AND METHODS

RELATED APPLICATIONS

The present application is a national phase under 35 U.S.C. § 371 of International Patent Application Serial No. PCT/US2017/035446, filed Jun. 1, 2017, entitled "Techniques For High Throughput Targeted Proteomic Analysis and Related Systems and Methods", which claims priority to U.S. provisional application No. 62/345,532, filed Jun. 3, 2016, entitled "Techniques For High Throughput Targeted Proteomic Analysis and Related Systems and Methods." The entire contents of these applications are incorporated herein by reference in their entirety.

BACKGROUND

Proteins play a critical role in the biological pathways of living organisms. Genes of an organism are frequently encoded to synthesize one or more proteins, which can cause various effects on cells and/or tissues within the organism. These effects can often differ between a healthy organism and a diseased organism, such that studying the protein makeup of cells and tissues, as well as protein function in these systems, can provide much information about the nature of a disease and/or condition. For example, protein biomarkers can be identified and be exploited to screen for a disease by testing for the presence or absence of the biomarkers.

Quantitative proteomics is one class of techniques for determining the amounts of proteins and/or peptides within a biological sample. Such techniques can involve gel electrophoresis, in which proteins are separated by mass whilst suspended in a gel; and/or mass spectrometry, in which proteins are fragmented and the fragments analyzed to identify the originating proteins. A subset of quantitative proteomics known as targeted proteomics seeks to focus on a narrow subset of samples' biological properties to achieve high sensitivity to that subset while maximizing throughput for a large number of input samples. In contrast, discovery-based proteomics techniques seek to identify a large number of the proteins in a biological sample, which are typically the most abundant proteins in the sample.

SUMMARY

According to some aspects, a kit is provided for performing an assay to determine a disease and/or condition state of an organism, the kit comprising a plurality of peptides proteotypic of a protein whose expression is characteristic of the disease and/or condition state, wherein the plurality of peptides are mass-tagged peptides.

According to some aspects, a composition of mass-tagged peptide molecules is provided having known molecular masses for use as mass spectrometry triggers, the composition comprising a population of first trigger molecules, wherein each first trigger molecule of the population of first trigger molecules includes a peptide portion bonded to a tag portion, the peptide portion being a first peptide and the tag portion being a first mass tag, and a population of second trigger molecules, wherein each second trigger molecule of the population of second trigger molecules includes a peptide portion bonded to a tag portion, the peptide portion being a second peptide, different from the first peptide, and the tag portion being the first mass tag.

According to some aspects, a composition of mass-tagged peptide molecules is provided having known molecular masses for use as mass spectrometry triggers, the composition comprising a population of trigger molecules, wherein each trigger molecule of the population of trigger molecules includes a peptide portion bonded to a tag portion, the tag portion being a first mass tag that is not isotopically substituted, wherein the peptide portion includes one or more isotopic substitutions, and wherein the trigger molecules of the population of trigger molecules are chemically identical to one another.

According to some aspects, a composition of mass-tagged peptide molecules is provided having known molecular masses for use as mass spectrometry triggers, the composition comprising a population of trigger molecules, wherein each trigger molecule of the population of trigger molecules includes a peptide portion bonded to a tag portion, the tag portion being a first mass tag that includes one or more isotopic substitutions, and wherein the trigger molecules of the population of trigger molecules are chemically identical to one another.

According to some aspects, a composition of mass-tagged peptide molecules is provided having known molecular masses, the composition including a first population of molecules for use as a mass spectrometry trigger and a second population of molecules for use to determine absolute quantities of peptides within samples in a mass spectrometry analysis, the composition comprising a first population of molecules, wherein each molecule of the first population of molecules includes a peptide portion bonded to a tag portion, wherein each molecule of the first population has a first mass, and wherein the molecules of the first population are chemically identical to one another, and a second population of molecules, wherein each molecule of the second population of molecules includes a peptide portion bonded to a tag portion, wherein each molecule of the second population has a second mass, different from the first mass, and wherein the molecules of the second population are chemically identical to one another and to the molecules of the first population.

According to some aspects, a method of preparing peptide samples for mass spectrometer analysis is provided by isobarically tagging the samples and combining tagged samples with preprepared mass-tagged peptide molecules having known molecular masses for use as mass spectrometry triggers, the method comprising obtaining a plurality of samples, each sample of the plurality of samples including molecules of a first peptide, reacting the molecules of the first peptide within each sample with an isobaric mass tag reagent, wherein different samples are reacted with different isobaric mass tag reagents, thereby producing isobarically tagged first peptide molecules within each sample such that isobarically tagged first peptide molecules within each individual sample and isobarically tagged first peptide molecules from different samples have the same mass and are chemically identical to one another, and isobarically tagged first peptide molecules in different samples are isotopically different, and combining the isobarically tagged first peptide molecules from each sample with a plurality of trigger molecules, wherein the trigger molecules are chemically identical to the isobarically tagged first peptide molecules within each sample, and wherein the trigger molecules each have a mass different from the mass of the isobarically tagged first peptide molecules.

The foregoing is a non-limiting summary of the invention, which is defined by the attached claims.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIGS. 1A-C depict an overview of targeted proteomic analysis including representative outputs at three separate stages of a mass spectrometry analysis, according to some embodiments;

FIG. 2A is a conceptual diagram of a mass tagged peptide, according to some embodiments;

FIG. 2B is a table providing illustrative masses of portions of the mass tagged peptide shown in FIG. 2A, according to some embodiments;

FIG. 3A is a schematic representation of a collection of different synthetic peptides each prepared to trigger a mass spectrometer for proteomic analysis of a respective peptide, according to some embodiments;

DETAILED DESCRIPTION

Figure 3B:
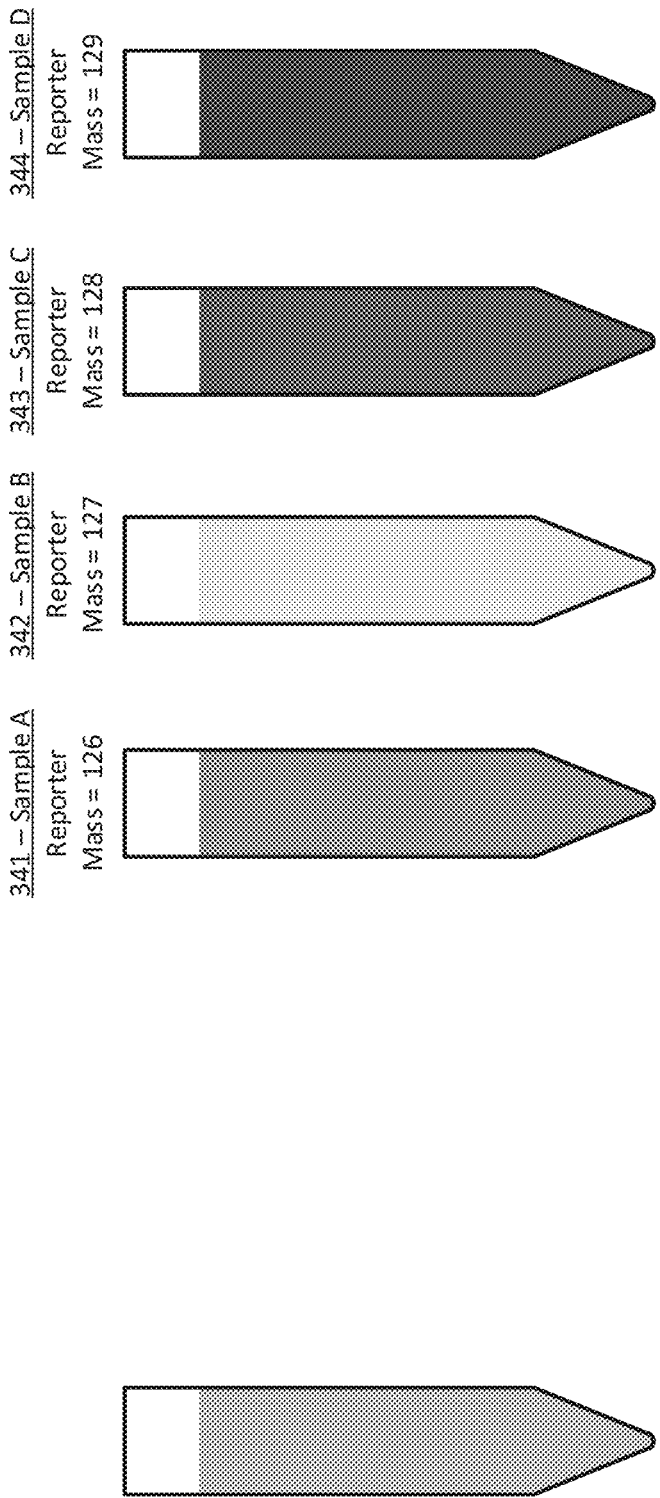
FIG. 3B is a schematic representation of the trigger peptides depicted in FIG. 3A and their relationship to tagged peptides from biological samples, according to some embodiments.

The inventors have recognized and appreciated that analysis of biological samples can be performed more quickly and more accurately by making available combinations of mass-tagged peptides as a kit to mix with biological samples on which a specific assay is to be performed. The kit includes tagged synthetic peptides with molecular masses offset from masses of sample peptides prepared for analysis. The sample peptides, once prepared for analysis using the kit, are also mass-tagged so that the tagged synthetic peptides in the kit are chemically identical to the prepared sample peptides.

Targeted proteomics has emerged as a powerful technology that enables absolute quantification at a much higher throughput than non-targeted (or "discovery-based") approaches. Targeted proteomics involves isolating particular input proteins and/or peptides, fragmenting those inputs and then isolating particular fragments for further analysis.

In contrast, discovery-based approaches may target a large number of proteins, and in some cases an entire proteome. As a result, discovery-based approaches may suffer from inconsistent reproducibility since the parameter space of the sample being analyzed under a discovery-based approach is large. In contrast, targeted proteomics allows for quantitative assays that are focused on answering particular questions about the biological makeup of a sample. Since the process in targeted proteomics may be directed to a narrow aspect of a proteome, the results may be significantly more reproducible than with a discovery-based approach.

It may be desirable in assays to perform a targeted proteomic analysis of multiple samples. However, in a targeted proteomic analysis of a complex sample, such as one containing a large number of peptides, there is a risk of producing fragments from different peptides that fall within the same isolation window. The isolation windows may thereby be selected to have a narrow width, but this in turn may cause the analysis to miss some of the target peptides if the isolation window is too narrow and/or not properly aligned to the target peptides. Thus, the analysis may suffer from poor collection efficiency of target peptides within a sample. This typically limits targeted proteomics to a single sample per injection, which limits throughput and sample coverage.

The inventors have recognized and appreciated that by including peptides engineered to act as a mass spectrometer trigger, the proper size and placement of an isolation window may be determined. The trigger peptides may have masses offset from corresponding target peptides from a sample and may be included in greater abundance than the expected abundance of the corresponding target peptides. Thus, the trigger peptides can be readily identified in a mass spectrometer analysis and, if the mass offset is known, the appropriate target isolation window may be identified. Moreover, this approach may allow the mass spectrometer to examine peptides injected into the mass spectrometer only when trigger peptides are identified; when they are not detected, the mass spectrometer may thereby perform less monitoring and/or analysis, which may lead to more efficient operation of the mass spectrometer.

The inventors have further recognized and appreciated that such trigger peptides provide for greatly increased throughput in a targeted proteomics analysis because such an approach allows multiple samples to be input to the mass spectrometer at the same time without causing the mass spectrometry analysis to become overwhelmed with data. In a conventional analysis, a mass spectrometer peak corresponding to a target peptide must be identified by its mass/charge ratio and abundance, which might be difficult if there is a lot of data produced in the mass spectrometer. However, since detection of a trigger peptide can be readily performed (e.g., due to the high abundance of the trigger peptide in the mass spectrometer input) and the corresponding target isolation window thereby identified, the triggering technique described herein mitigates other peptides and/or peptide fragments which might be present in the mass spectrometer data from interfering with the analysis.

Furthermore, samples may be prepared so that peptides of interest within the samples are isobarically tagged in such a way as to all have the same mass as one another (i.e., are isobaric), while varying the placement of isotopes within the isobarically tagged peptide molecules so that they are not isotopically identical across samples. Since they are chemically identical, the isobarically tagged peptide molecules will elute simultaneously, and once fragmented within the mass spectrometer the sample fragments may be distinguished from one another (that is, the originating sample may be identified) using knowledge of how each sample's isobarically tagged peptide molecules were isotopically different from one another. Peptides may thereby be multiplexed in two ways: first, by providing samples containing different peptides as a single combined input to the mass spectrometer; and second, by determining abundances for multiple samples from a single pass through the mass spectrometer.

As used herein, molecules, molecular fragments and/or ions that are considered "chemically identical" to one another are formed from the same chemical elements and exhibit the same chemical structure, although isotopes of one or more of those elements may differ. For instance, as used herein phenol ($^{12}C_6H_5OH$) may be considered "chemically identical" to phenol in which one or more of the hydrogen atoms is the deuterium isotope and/or one or more of the carbon atoms is the $^{13}C$ isotope (e.g., $^{13}C_6H_5OH$).

According to some embodiments, isobarically tagged synthetic peptides may be provided as input to the mass spectrometer in addition to the samples. As described above, these "trigger peptides" may provide for greater efficiency and accuracy in a targeted proteomic analysis by allowing effective identification and isolation of peptides present in sample. The trigger peptides are arranged to have a different mass from the same peptides present in each sample, yet have the same chemical structure so as to elute along with a corresponding peptide in the sample. It may be preferable that the mass of a trigger peptides is substantially different than the mass of a corresponding peptide in the sample to simplify triggering, although in general so long as the masses of the trigger and sample populations are different and known, the trigger molecules may aid identification of the corresponding peptides in the sample, even when their amounts are small.

Isobarically tagged synthetic peptides that are used as trigger molecules may be prepared in numerous ways, and may have a mass either greater or less than that of a corresponding peptide in the sample. According to some embodiments, a trigger molecule may be prepared in at least one of three broad approaches. In a first approach, the trigger molecules may be produced by synthesizing a peptide having some canonical (e.g., naturally occurring) mass and then attaching an isobaric mass tag (or, in some cases, more than one mass tag) to each peptide molecule. In a second approach, the first approach may be followed in addition to a step of modifying the mass of the peptide portion of the trigger molecules (i.e., the "non-tag" portion). In a third approach, the first approach may again be followed in addition to a step of modifying the mass of the tag portion of the trigger molecules relative to the mass of tag portions used to tag a corresponding peptide in the sample. Said mass modification in the second or third approaches may be performed by, for example, performing isotopic substitutions of either or both portions of the trigger molecules to modify the mass of the molecules without changing their chemical structure (e.g., relative to a natural or otherwise commonly occurring form of a corresponding peptide in the sample). Alternatively, synthetic trigger molecules may be synthesized with heavier isotopes than are present in corresponding peptides in samples, then tagged with the same tag as is used to tag the corresponding peptides in the samples. In some use cases, how the trigger molecules are prepared may depend on how the samples have been prepared since, to perform the above-described triggering technique, it is only desirable that the trigger molecules have a different mass from corresponding peptides in the sample whilst being chemically identical due to the presence or absence of heavy isotopes.

As discussed above, fragments of peptides from different samples may be distinguished from one another during mass spectrometry analysis, even though the samples were provided together as an input to the mass spectrometer. In a final stage of a mass spectrometer analysis, tagged peptides from different samples may be fragmented into a number of fragments whose masses are known (previous fragmentation may also have occurred in the mass spectrometry process). For example, the masses may be known because the mass tags are designed to fragment in particular locations, thereby producing known fragments. If these fragments are isotopically different from one another due to the isotopic differences between the tagged samples from which the fragments originated, and if those isotopic differences are unique to each sample, the sample that produced each fragment can be identified because the fragments will have masses that map directly to the originating samples. For example, two peptide samples may each be tagged with a mass tag of a particular mass whilst the distribution of masses within the mass tag of the first sample is different from that of the second sample. Accordingly, fragments produced in a particular stage (e.g., a final stage) of a mass spectrometer may include two chemically identical portions of the mass tag from each of the two samples with different masses that can be used to identify which sample produced which type of fragment.

According to some embodiments, fragmentation of peptides in a mass spectrometer may include one or more quality assurance filters. According to some implementations, such filters may include a mass accuracy filter which selects a fragment for further analysis only if the fragment has a mass within a particular window of its expected mass (e.g., within ±5 ppm of an expected mass, within ±10 ppm of an expected mass, etc.). According to some implementations, quality assurance filters may include an isobaric interference filter that selects fragments for further analysis only if their abundance is within a particular range of ratios relative to one or more other fragments expected from the same peptide. According to some implementations, quality assurance filters may include a purity of isolation filter that selects fragments for further analysis only if the fragments within the selected mass window include purity of the fragments of interest above some threshold amount. Any number of quality assurance filters, including the illustrative filters described above and/or other filters may be used in combination during a mass spectrometry analysis.

According to some embodiments, isobarically tagged synthetic peptides may be provided as input to the mass spectrometer in addition to the samples. The isobarically tagged synthetic peptide molecules may have the same mass as corresponding peptides from the samples, yet may be isotopically different from each of the peptides from the samples. The quantification peptides may be included in addition to the trigger peptides, or may be used in the absence of the trigger peptides. The quantification peptides may be provided in a known quantity and may be isotopically different from corresponding peptides from the samples such that fragments originating from the quantification peptides may be distinguished from fragments originating from the samples within the mass spectrometer. Since the abundance of the quantification peptides is known, an absolute abundance of corresponding peptides from the samples may be determined by comparing the relative abundances of fragments produced from each source.

Following below are more detailed descriptions of various concepts related to, and embodiments of, techniques for multiplexed proteomic analysis. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1A depicts an overview of targeted proteomic analysis including representative outputs at three separate stages of a mass spectrometry analysis, according to some embodiments. The illustrative analysis 100 shown in FIG. 1A uses a tandem mass spectrometer having three analyzers, with an analyzer present in each of stages $MS^1$, $MS^2$ and $MS^3$, of which graphical representations are provided in FIG. 1A and labeled as stages 120, 130 and 140, respectively. In the $MS^1$ stage, trigger peptides and corresponding peptides in a sample are identified, then fragmented and analyzed in the $MS^2$ stage. In the $MS^2$ stage, fragments thereby produced are selected and further fragmented then analyzed in the $MS^3$ stage. As discussed above, at one or more stages of the mass spectrometer analysis, fragments originating from different sample peptides may be distinguished by having different masses. In the example of FIG. 1A, this stage is the $MS^3$ stage.

In the example of FIG. 1A, a mixture 110 containing biological peptide samples and trigger peptides is used as an input to the analysis; as discussed below, portions of this input are separately introduced to the mass spectrometer. As described above, according to some embodiments a number of biological samples may be prepared by mass tagging the samples using a set of mass tags that are all isobaric and "chemically identical," but, each tag in the set has a different arrangement of isotopes. Each sample is tagged with an isotopically different mass tag. In this way, molecules of a given tagged peptide initially have the same mass in each sample but differ across the samples in their isotopic compositions. This difference in isotopic composition can be detected in fragments resulting from the samples, such that peptides that were tagged by each tag can be differentiated at later stages of the MS analysis, allowing the relative abundance of a particular peptide in each sample to be identified through MS analysis. These tagged peptides may be provided together as an input to a proteomic analysis as shown in FIG. 1A.

Moreover, in the example of FIG. 1A, trigger peptides are also included in the input mixture 110. As described above, trigger peptides are synthetic peptides tagged using the same mass tag as was used to tag the corresponding peptides from the samples yet having a different molecular mass than the samples. The trigger peptides are used as a trigger in the depicted analysis by producing a readily identifiable (e.g., highly abundant) peak in the mass spectrometer $MS^1$ data, allowing identification of an isolation window from which peptides are selected for further analysis.

The combined mixture 110 in the example of FIG. 1A therefore includes, for a given type of peptide, a mixture of molecules of the peptide that are each associated with one of a number of biological samples, and synthesized molecules of the peptide to be used as a mass spectrometer trigger. Each of the molecules for the given peptide are chemically identical to one another, yet the trigger peptide molecules have a different mass relative to the peptides from the biological samples. The peptide molecules from different samples have different isotopic compositions despite having the same molecular mass (which could mean a different collection of isotopes or the same collection of isotopes arranged differently).

In the example of FIG. 1A, a number of different peptides are combined into an input to analysis 100. To conduct a targeted proteomics analysis, it may be desirable to examine each type of peptide in turn for the plurality of samples using the mass spectrometer. However, such an analysis may demand that a peptide type of interest is substantially separated from the remainder of the inputs for analysis. The inventors have recognized and appreciated that such separation may be achieved via the above-described arrangement, since input 110 may be arranged in a solution such that chemically identical peptides elute simultaneously from the input 110 and are input to the mass spectrometer. As such, each type of peptide present in input 110 may elute in turn and enter the mass spectrometer for analysis substantially independently of other peptide types present in input 110. Thus, process 100 may perform a multiplexed analysis of input 110 in two ways: (i) by peptide type via separate elution into the mass spectrometer; and (ii) by eluting peptides from multiple biological samples that can be distinguished from one another in the mass spectrometer.

For clarity, stages 120, 130 and 140 of FIGS. 1A-C illustrate the mass spectrometry process for a single peptide type eluted from the input 110 into the mass spectrometer. An analysis utilizing the same input 110 may therefore repeat stages 120, 130 and 140 for additional peptides of interest. Note that in each of stages 120, 130 and 140 additional molecules and/or molecular fragments will in practice be present in the depicted spectral data, but for clarity only illustrative data relevant for explanation of the analysis techniques are depicted.

According to some embodiments, input mixture 110 may be provided to a liquid chromatography system so that peptide types elute from solution by adjusting the pH of the solution. The eluted peptides can be provided to the mass spectrometer via an electrospray or other suitable means.

In stage 120, the peptide molecules eluted from input 110 are examined in the mass spectrometer to identify the peptides of interest. As a result of the mass tagging process described above, the trigger peptides 121 have a first mass that is a known offset from the mass of the tagged peptide samples 122. According to some embodiments, the mass spectrometer may be configured to identify the peptide samples 122 by identifying the trigger peptide in the mass spectrometer data and then using the known offset to identify an isolation window in which the corresponding peptide samples are expected to appear. In some cases, the peptide sample 122 may appear in sufficient abundance that they can be readily identified. However, in some cases they may be measured in a sufficiently low abundance that might ordinarily make detection difficult or impossible. In at least these cases, the use of the trigger peptides can allow detection of the peptide samples since the peptide samples themselves need not be identified directly to be isolated and passed to the next stage of the mass spectrometer. Rather, an isolation window (being a range of masses around the expected mass of the peptide samples) can be identified from identification of the trigger peptides in the mass spectrometer data and by applying the known offset to the measured mass of the trigger peptides. In some embodiments, the trigger peptides may be supplied in an abundance known to be greater as an expected abundance of the corresponding peptide in the samples so that the trigger peptide may be readily identified in the $MS^1$ data. For example, the ratio of trigger peptide abundance to expected abundance of the corresponding peptide in the samples may be between 5 and 100, or between 20 and 80, or between 40 and 60.

Irrespective of how the isolation window is identified in stage 120, in the example of FIG. 1A, the mass spectrometer performs fragmenting of the contents identified as being within this isolation window and the mass/charge of the resulting fragments is measured in the $MS^2$ stage. For example, the mass spectrometer may be programmed to tune an ion trap (e.g., an ORBITRAP®) to isolate the selected peptides 122 from the isolation window identified in stage 120 so that the selected samples can be fragmented in the $MS^2$ stage.

Illustrative results of the $MS^2$ stage are shown in FIG. 1B, and include portions of the peptide samples measured having various masses, which each represent different fragments of the peptide molecules after fragmentation. As noted above, only data pertinent to this discussion is shown in the illustrative figure and in general much more data generated from a number of different fragments might be expected to be captured in such an analysis. Moreover, while numerical values on the m/z axes in stages 120, 130 and 140 are not shown for clarity, the m/z values being measured are progressively getting smaller from stage 120 to stage 130 to stage 140 due to the fragmentation of larger molecules/ions into smaller fragments.

In stage 130, one or more isolation windows are selected in order to select target fragments (e.g., ions) known to contain one or more portions of the sample peptide molecules that are isotopically different across samples. These isolation windows may be selected based on data about the peptide type being analyzed, the type of mass tag attached to the peptide and/or knowledge of how the tagged peptide fragments in a mass spectrometer.

According to some embodiments, stage 130 may include application of one or more quality assurance filters. A mass spectrometer may be programmed to examine data produced from the $MS^2$ stage, for example, and make a determination of which fragments to isolate for further analysis. Such a determination may be based upon data about the peptide being analyzed, the data produced from the $MS^2$ stage, and/or data associated with a particular quality assurance metric.

According to some implementations, such filters may include a mass accuracy filter which selects an $MS^2$ fragment for further analysis only if the fragment has a mass within a particular window of its expected mass (e.g., within ±5 ppm of an expected mass, within ±10 ppm of an expected mass, etc.). Selection of the isolation window size may in some cases depend on the peptide type being analyzed and/or upon the particular target fragment being considered. Isolation window data can be stored within a mass spectrometer device or be otherwise accessible to the device during analysis 100.

According to some implementations, quality assurance filters applied during stage 130 may include an isobaric interference filter that selects fragments for further analysis only if their abundance is within a particular range of ratios relative to one or more other fragments expected from the same peptide. For instance, the abundance of one of the data peaks shown in FIG. 1B stage 130 may be compared to one or both of the other data peaks in the same dataset, and only if the ratio of the peaks is within a particular range are the fragments selected for further analysis. Alternatively, or additionally, abundance of a data peak in stage 130 may be compared with other peaks not included in one of the isolation windows (these peaks are not shown in FIG. 1B). Data describing the acceptable ranges of ratios of expected fragment abundances can be stored within a mass spectrometer device or be otherwise accessible to the device during analysis 100.

According to some implementations, quality assurance filters applied during stage 130 may include a purity of isolation filter that that selects fragments from the $MS^2$ for further analysis in the $MS^3$ stage only if the fragments within the selected mass window include purity of the fragments of interest above some threshold amount. Data describing one or more acceptable purity thresholds can be stored within a mass spectrometer device or be otherwise accessible to the device during analysis 100.

In the example of FIGS. 1A-C, the mass spectrometer performs further fragmenting of the contents identified as being within the isolation window(s) in stage 130, and the mass/charge ratio of the resulting fragments are measured in stage 140. Once again, only data pertinent to this discussion is shown in the illustrative figure so that the targeted fragments shown in stage 140 can be illustrated clearly. In this stage, isotopically different pieces of the sample peptides have been separated from one another and appear as substantially distinct peaks in the $MS^3$ data. As discussed below, the mass tags to which the peptides are bonded may include comparatively weak bonds around a portion of the mass tag that is isotopically different amongst the samples' mass tag so that fragmentation of the molecules will tend to produce fragments comprising those portions. Accordingly, since the masses of those portions are known, they can be identified and correlated with their respective samples in the $MS^3$ stage of analysis 100.

The relative abundances of the fragments identified in stage 140 are indicative of the relative abundances of the peptide type being analyzed within each of the samples in input 110. If the absolute abundance of one of the fragments is known, the absolute abundances of the other fragments can be determined. As discussed above, one way to achieve this result is to include a synthetic peptide having the same mass as molecules of the peptide type being analyzed yet isotopically different from instances of that peptide type within the samples. While this approach is not depicted in FIG. 1C, this would provide an additional data peak in stage 140 that represents a known absolute abundance. The absolute abundances of the other peaks can then be determined based on the relative peak sizes.

The synthetic peptide used for determining absolute abundance of peptides may be a separately added peptide. Alternatively, or additionally, the peptide used to determine absolute abundances of the fragments identified in stage 140 may be the trigger peptide 121. If the absolute abundance of the trigger peptides is known, the total abundance of the peptide samples can be determined. If the amount of trigger peptide for the current peptide being analyzed is known, therefore, the total abundance of all of the data peaks in stage 140 can be inferred from the $MS^1$ data. It may be desirable when using the trigger peptide in such a way to supply the trigger peptides in an amount greater than, but somewhat comparable to, the amount of corresponding peptides in the samples. For example, the ratio of trigger peptide abundance to expected abundance of the corresponding peptide in the samples may be between 5 and 50, or between 10 and 30, or between 15 and 25.

FIG. 2A is a conceptual diagram of a mass tagged peptide, according to some embodiments. Molecule 200 illustrates one possible approach to mass tagging a peptide for use in a proteomic analysis, such as analysis 100 shown in FIGS. 1A-C. In the example of FIG. 2A, a peptide 210 is bonded to a mass tag 220. The mass tag 220 includes two portions, a reporter portion 221 and a balance portion 222. According to some embodiments, the mass tag include, but is not limited to, mass tags such as $TMT_0$, $ITRAQ_0$, iTRAQ, $CMT_0$, fully $^{13}C$ labeled lysine or arginine, and super heavy TMT.

As discussed above, when mass tagging a peptide for a proteomic analysis as described herein, it may be advantageous to mass tag peptides from different samples such that the resulting tagged peptides have the same mass but are isotopically different. This may be achieved in molecule 200 by varying the isotopes that make up the peptide 210, the reporter 221 and/or the balance 222 within each sample. Synthetic trigger peptides and/or quantification peptides may also be created from a synthetic peptide 210 and mass tag 220. The mass of the trigger peptides can be varied by selecting the isotopes that make up the peptide 210, the reporter 221 and/or the balance 222 tagged trigger peptides so that the mass is different from corresponding peptides from the sample that have been, or will be, prepared. Quantification peptides can be altered to utilize different isotopes than corresponding peptides from the sample that have been, or will be, prepared whilst having the same mass as the corresponding peptides from the sample. Generally speaking, the isotopic composition of molecule 200 may be varied by adjusting the isotopic composition of the peptide 210, the mass tag 220, or both the peptide 210 and the mass tag 220, so long as a suitable fragment of the molecule can be produced in a mass spectrometer that identifies the molecule as being distinct from other chemically identical yet isotopically different molecules.

According to some embodiments, a mass tag 220 may be selected for each sample wherein the selected mass tags have the same mass as each other but have different reporter and balance masses, whilst being chemically identical. If the resulting molecule 200 tends to fragment along the bonds 215 and 224, the reporter ions produced during mass spectrometry fragmentation may be measured (e.g., in the $MS^3$ stage shown in FIG. 1C). Since there is a one-to-one mapping between the reporter mass and a particular biological sample, such an arrangement facilitates measurement of the abundance of the samples by measuring the abundances of the reporter ions.

It will be appreciated that the diagram of FIG. 2A is intended to demonstrate broadly how a mass tagged peptide molecule may be structured and that additional parts of the molecule may exist and are not shown in FIG. 2A. Furthermore, in some implementations, multiple mass tags (which may be the same or may be different) may be bonded to a single peptide.

FIG. 2B is a table providing illustrative masses of portions of the mass tagged peptide shown in FIG. 2A, according to some embodiments. In the example of FIG. 2B, the mass of the naturally occurring peptide is labeled $M_P$. As referred to herein, a "naturally occurring" instance of a peptide includes one that exists in nature without artificial aid, such as an instance of the peptide found in the human body. In FIG. 2B, three samples are presented, which have the same molecular mass and are chemically identical yet include different reporter and balance masses from one another. Masses are presented in the table in approximate atomic mass units. When provided as input to a proteomic analysis such as analysis 100 shown in FIGS. 1A-C, the reporter portions of the molecules may be separated via fragmentation in a mass spectrometer and the corresponding sample identified.

In addition, in the example of FIG. 2B, trigger molecules are prepared from atoms within the peptide with heavier isotopes such that the trigger molecules have a mass that is 40 atomic mass units greater than the mass of the sample molecules. Note that, as discussed above, trigger molecules can in general have a mass that is either greater or less than the mass of prepared samples so long as the offset is known.

In practice, to prepare for a proteomic analysis, samples may be prepared in view of preprepared trigger peptides, or alternatively, trigger peptides may be prepared in view of preprepared samples. For instance, a kit containing prepared trigger peptides may be supplied with information indicating: the mass tag used to produce the trigger peptides, the mass of the trigger peptides for each type of peptide provided, and/or an amount (e.g., volume, concentration) of the trigger peptides supplied for each type of peptide provided. A user may then utilize the information supplied with the kit to prepare samples to be mixed with the supplied trigger peptides. For example, the user may tag corresponding peptides from a sample using the same mass tag as was used to tag the supplied trigger peptides based on the information.

According to some embodiments, a kit may be prepared for use in performing an assay to identify a disease and/or condition of an organism (e.g., diagnosing cancer in a patient). To identify the disease and/or condition, relative amounts of specific peptides may be determined. If a peptide uniquely identifies a specific protein (i.e., it is proteotypic), its abundance in a biological sample taken from an organism can indicate something about the disease and/or condition of the organism (e.g., because certain genes being up- or down-regulated impacts the amount of specific proteins present). By determining the abundances of a number of such peptides in such a panel, therefore, a disease and/or condition may be identified. The kit may include trigger peptides for each of these peptides in the panel to allow a user to prepare suitable biological samples and mix the results with the kit to prepare an input to a mass spectrometer.

As an illustrative example, FIG. 3A is a schematic representation of a kit containing peptides prepared to act as triggers for a proteomic analysis, according to some embodiments. Although the kit in FIG. 3A is depicted as a test tube, the contents of the kit may be supplied in any suitable form, including by liquid, powder, and/or isolated peptides to be reconstituted in a buffer.

In the example of FIG. 3A, the kit 310 is a mixture of three peptide types, referred to in the figure as "Synthetic Peptide 1," "Synthetic Peptide 2' and "Synthetic Peptide 3," where each of the three peptide types has been tagged with the same mass tag, "Mass Tag A." While it is not a requirement that the same mass tag be used with each of the trigger peptides, it may be convenient to do so, so that each corresponding peptide from the samples can be tagged using the same mass tag. Otherwise, different peptides within each sample would need to be tagged with different tags to use the supplied kit 310 as a set of triggers.

The kit 310 may include instructions that identify mass tag A, identify the molecular mass of each of the tagged peptides 301, 302 and 303, identify the three synthetic peptide types and/or identify an amount (e.g., volume, concentration, moles) of each of the tagged peptides 301, 302 and 303 present in the kit. Such instructions may be included in the kit in any suitable manner, including by a label or other printed matter affixed to one or more components of the kit, documentation supplied with the kit and/or stored in electronic form on an article associated with the kit, which may include information that links to a source of the instructions (e.g., a barcode, an Internet URL, etc.).

FIG. 3B is a schematic representation of the trigger peptides depicted in FIG. 3A and their relationship to tagged peptides from biological samples, according to some embodiments. As discussed above, biological samples may be prepared based on trigger peptides in a supplied kit in order to be chemically identical to the trigger peptides yet have a different mass to the trigger peptides. The difference between the two masses are shown in FIG. 3B as the "trigger offset." The trigger peptides may be either lighter or heavier than masses of corresponding peptides from the samples, and FIG. 3B is an example of an implementation in which the trigger peptides are lighter. The four biological samples 341-344 shown in FIG. 3B have different reporter portion masses, thus enabling identification of which sample a reporter ion came from when determining masses of the reporter ions in a mass spectrometer. The samples 341-344 were prepared in a known way in order to be compatible with the trigger peptides; that is, each peptide from a given sample is prepared to be chemically identical to a corresponding trigger peptide. Such preparation may be performed based on instructions included within the kit of which trigger peptides 310 are a component.

Figure 3C:
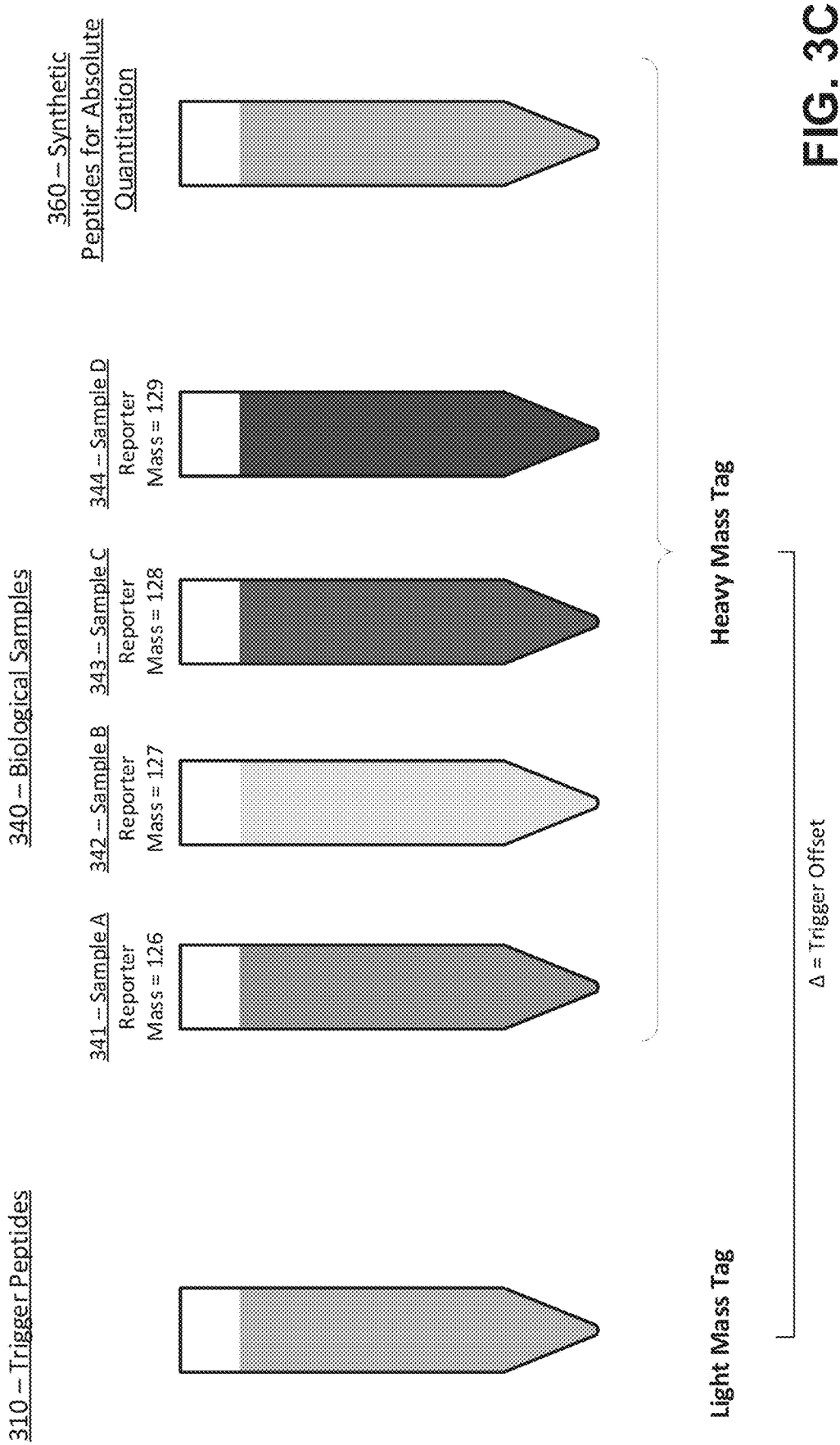
FIG. 3C is a schematic representation of the trigger peptides and tagged peptides from biological samples as shown in FIGS. 3A and 3B, respectively, and synthetic peptides tagged for absolute quantitation, according to some embodiments.

FIG. 3C is a schematic representation of trigger peptides and tagged peptides from biological samples as shown in FIGS. 3A and 3B, respectively, with synthetic peptides tagged for absolute quantitation, according to some embodiments. As discussed above, synthetic peptides having the same mass as corresponding peptides from the samples yet being isotopically different from those peptides may be useful to determine absolute quantities of the corresponding peptides from the samples during analysis. In order to be used as input to a proteomic analysis, peptides of a given type taken from the trigger peptides 310, prepared biological samples 340 and quantification peptides 360 may be chemically identical to one another.

According to some embodiments, a kit may comprise the trigger peptides 310 and the quantification peptides 360 in addition to instructions so that a user can prepare samples 340 for use with the peptides included within the kit and to analyze results of measuring the samples within a mass spectrometer. For instance, a kit containing trigger peptides 310 and quantification peptides 360 may be supplied with information indicating: the mass tag used to produce the peptides 310 and 360, the mass of the trigger peptides for each type of peptide provided, the mass of the quantification peptides for each type of peptide provided, an amount (e.g., volume, concentration) of the trigger peptides supplied for each type of peptide provided, and/or an amount (e.g., volume, concentration) of the quantification peptides supplied for each type of peptide provided. A user may then utilize the information supplied with the kit to prepare samples to be mixed with the supplied trigger peptides and quantification peptides.

Figure 4:
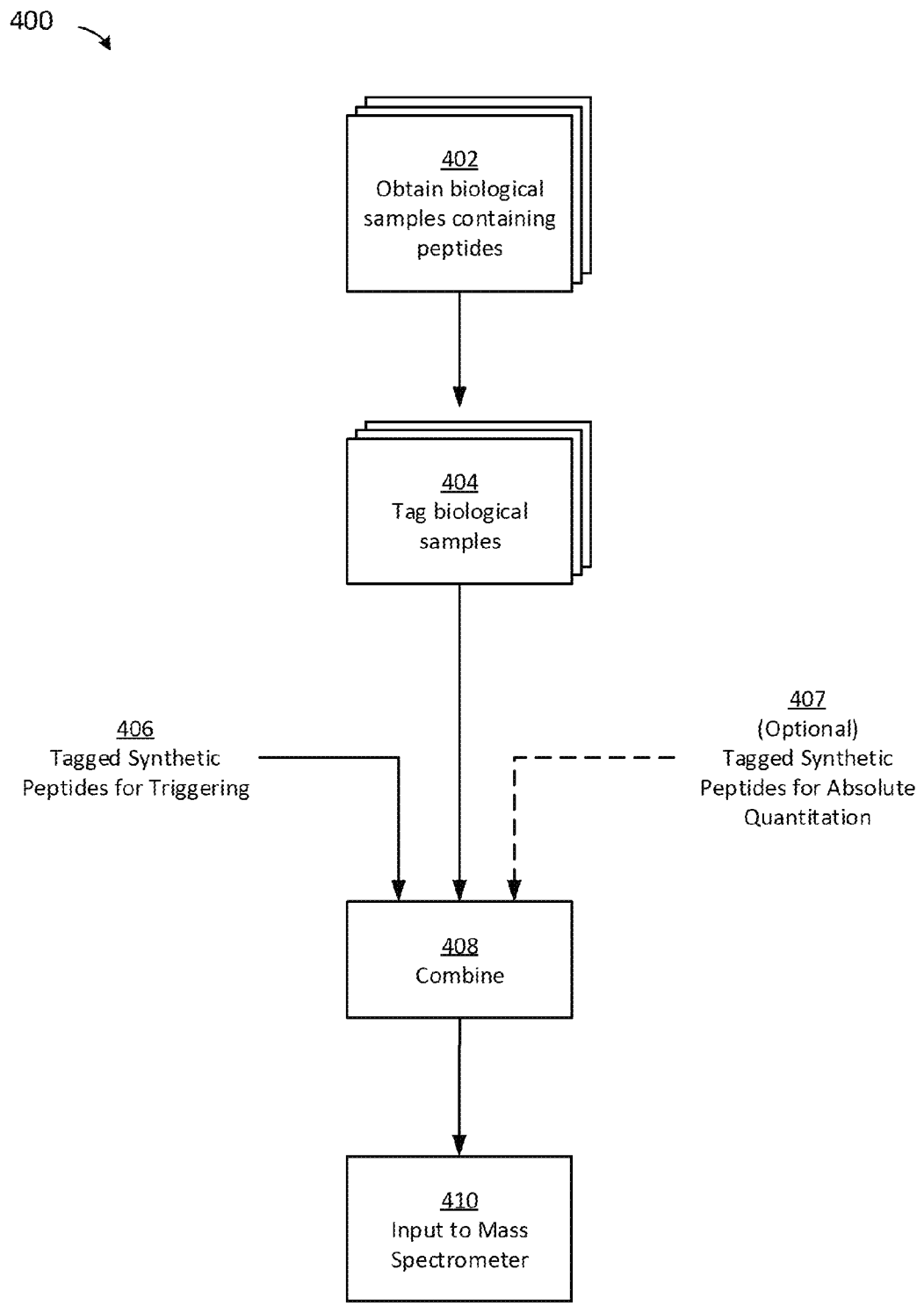
FIG. 4 is a flow chart of a method of preparing samples for proteomic analysis using a kit of tagged synthetic peptides, according to some embodiments.

FIG. 4 is a flow chart of a method of preparing samples for proteomic analysis using a kit of tagged synthetic peptides, according to some embodiments. In method 400, a user prepares biological samples for proteomic analysis by combining the samples with synthetic peptides from a kit, which may include trigger peptides and/or quantification peptides. The resulting combination can then be supplied as input to a suitable proteomic analysis, such as analysis 100 shown in FIGS. 1A-C.

In act 402, the user obtains biological samples containing peptides. These biological samples may be obtained from any suitable source, and may be, for example, cells and/or tissues from a patient, from a laboratory animal, or may comprise patient xenograft samples. An aspect of act 402 may include preparation of one or more of the samples for use in the proteomic analysis, which may comprise steps such as, but not limited to, performing lysis, protein purification, and/or digestion upon a sample.

In act 404, the biological samples are tagged with a mass tag. The same mass tag may be applied to each of the samples. Illustrative mass tags that may be used in method 400 include, but are not limited to, $TMT_0$, $ITRAQ_0$, iTRAQ, $CMT_0$, fully $^{13}C$ labeled lysine or arginine, and super heavy TMT. The mass tag may be selected based on instructions included with a kit with which the prepared tagged samples are to be combined. Trigger peptides of the kit may have been previously prepared using said mass tag. Furthermore, the particular isotopic composition of each sample may be engineered to be different from one another, and also different from tagged synthetic peptides for absolute quantitation 407 to be added, should the kit include them.

In act 408, the tagged biological samples produced in act 404 are combined with tagged synthetic peptides for triggering 406, and optionally, with tagged synthetic peptides for absolute quantitation 407. According to some embodiments, the combination may be mixed with other materials (e.g., a buffer) in order to prepare the mixture for injection into a mass spectrometer. For example, the combination of tagged biological samples produced in act 404, tagged synthetic peptides for triggering 406, and optionally, tagged synthetic peptides for absolute quantitation 407, may be further combined with water, a water-miscible solvent (e.g., acetonitrile, acetone, methanol), an acid (e.g., trifluoroacetic acid, formic acid), or combinations thereof. The resulting mixture can be supplied as an input to a mass spectrometer in act 410. Where liquid chromatography is utilized to input the mixture to a mass spectrometer in act 410, an amount of solvent in the buffer in which the peptides have been mixed may be increased over time to elute the peptides into the mass spectrometer.

As an illustrative example of preparing samples for proteomic analysis techniques as described herein, and to illustrate the value of a kit prepared for a targeted analysis, the following case study will be described. The MAPK pathway is known to play a critical role in several cancers—particularly, breast and melanoma, where one or more members of this pathway are either over-activated or over-expressed. To determine which node of the pathway may be altered, one may want to profile the absolute and relative abundance of MAPK pathway members by monitoring unmodified and/or phosphorylated peptides of those proteins in patient xenograft samples.

A kit could be supplied containing proteotypic peptides for each of the proteins of interest. Each of the peptides may be included in the kit in two forms: a trigger peptide and a quantification peptide—though in some embodiments only one or the other will be in the kit. The kit's peptides may be labeled with an appropriate TMT (isobaric) tag. Further, the kit may include information indicating the amount of the trigger peptide and quantification peptide for each of the proteins of interest present in the kit (e.g., the maker of the kit may have amino acid analyzed the peptides so that the amount of peptides in each produced vial is known, e.g., 500 pmol/vial).

To measure levels of the proteins of interest in 9 xenograft samples, a user could perform lysis, protein purification, digestion and TMT labeling on those samples and then spike in an appropriate amount of the trigger and quantification peptides into the samples prior to loading them onto an instrument for analysis. How much of the peptides from the kit to include may, in some cases, be indicated by the kit, which can be determined in advance based on the expected abundance of each of the target peptides. The kit may be arranged to include trigger and quantification peptides in quantities designed to have a suitable quantity relative to target peptides expected in the sample. The quantification peptide could be labeled with a TMT channel not used by the 9 xenograft samples, to complete a 10-plex TMT analysis. One example would be the GTPase activating protein, NF1. Two peptides that could be chosen to analyze this protein are VAQLAVINSLEK and LILNYPK. These peptides act as surrogates for the protein itself, and each node of the pathway would have its own pair of peptides. In general, many more peptides may be included in a panel for such an analysis, such as between 5 and 500 peptides, or between 50 and 300 peptides, or between 100 and 200 peptides. Peptides selected may have any suitable length, such as a length of at least 5 amino acids and no more than 50 amino acids, or a length of at least 10 amino acids and no more than 40 amino acids, or a length of at least 20 amino acids and no more than 30 amino acids.

More generally, to select a panel of peptides to analyze in a given assay, a pathway may be identified that is known to relate to a particular disease state. One or more proteins associated with that pathway may be identified and peptides associated with the one or more proteins selected. In some cases, peptides selected may be proteotypic of one or more of the identified proteins. A kit may be produced that includes the peptides selected for the panel, wherein the peptides include at least trigger peptides and information indicating the amount of the trigger peptide for each peptide type of the panel. An assay that analyzes multiple biological samples to determine abundances of each of the peptides of the panel may then be performed in a single run of the mass spectrometer as described herein.

In some embodiments, a protein selected to analyze in a given assay is a protein from a pathway (e.g., a signaling pathway) involved in cancer. For example, the protein may be in a protein involved in a MAPK/ERK pathway, an AKT signaling pathway, a vascular endothelial growth factor (VEGF) pathway, an epidermal growth factor (EGF) signaling pathway, a p53 pathway, and/or a hypxia-inducible factor (HIF) pathway. However, other signaling pathways involved in cancer are within the scope of this disclosure. In some embodiments, the protein is involved in an MAPK/ERK signaling pathway. Exemplary proteins from a MAPK/ERK signaling pathway include, but are not limited to, Ras, Raf, MEK, ERK, MAPK, MNK and dCREB. In some embodiments, the protein is involved in an AKT signaling pathway. Exemplary proteins from an AKT signaling pathway include, but are not limited to, Ack1, Src, PTK6, IKKε, TBK1, DNA-PK, PTEN, SHIP, PPARβ/δ, TNFα, PP2A, CTMP and IRS-1. In some embodiments, the protein is involved in a VEGF signaling pathway. Exemplary proteins from a VEGF signaling pathway include, but are not limited to, VEGF-A, VEGF-B, VEGF-C, VEGF-D, PIGF, and VEGFR (e.g., VEGFR-1 and VEGFR-2). In some embodiments, the protein is involved in an EGF signaling pathway. Exemplary proteins from an EGF signaling pathway include, but are not limited to, EGFR, EGF, HB-EGF, TGF-α, AR, EPR, BTC, NRG1, NRG2, NRG3, NRG4 GRB2 and SOS. In some embodiments, the protein is involved in a p53 signaling pathway. Exemplary proteins from a p53 signaling pathway include, but are not limited to, p53, and MDM-2. In some embodiments, the protein is involved in a HIF signaling pathway. Exemplary proteins from a HIF signaling pathway include, but are not limited to HIF-1α, HIF-1β, HIF-2α, HIF-2β, HIF-3α, HIF-3β, VHL and VEGF.

Any peptides associated with any identified proteins from the above list or otherwise may be selected for inclusion in a panel for an assay, and a kit may be prepared including trigger peptides for each of the selected peptides. At least one of the selected peptides may be proteotypic of one or more of the identified proteins.

Figure 5:
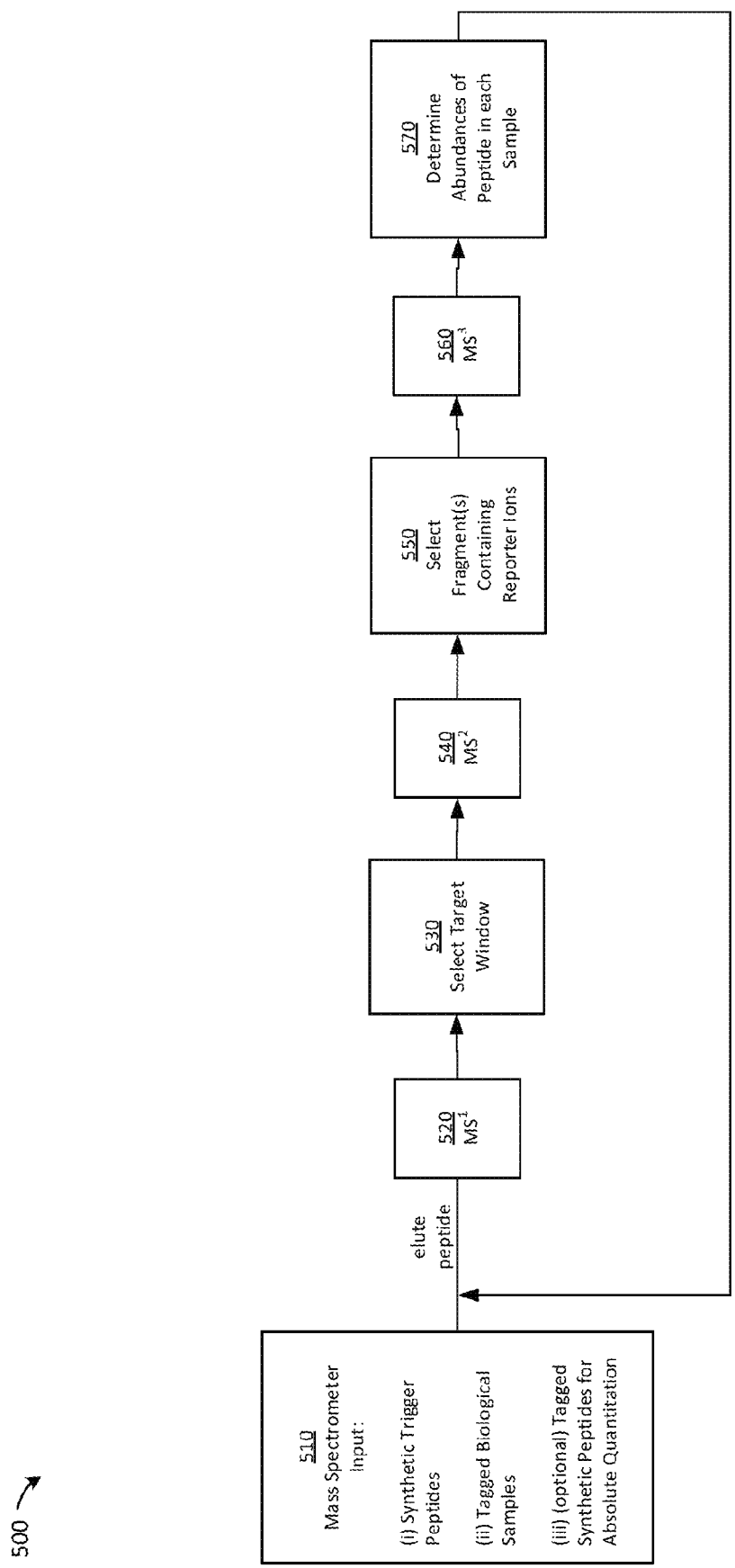
FIG. 5 is a flow chart of performing proteomic analysis using a mass spectrometer, according to some embodiments.

FIG. 5 is a flow chart of performing proteomic analysis using a mass spectrometer, according to some embodiments. In method 500, a mixture prepared as per method 400 described above in relation to FIG. 4 is provided as input to a mass spectrometer. For instance, the mixture may be input to a column that is part of a liquid chromatograph configured to provide input from the chromatograph to the mass spectrometer (e.g., via electrospray). In act 510, a particular peptide type (or set of peptide types) present within the input is separated from the remainder of the input and input to a mass spectrometer.

According to some embodiments, peptide types may be progressively separated from an input mixture via liquid chromatography, in which peptides are loaded onto a column in a buffer containing an acid (e.g., trifluoroacetic acid or formic acid) and an organic solvent (e.g., acetonitrile or methanol). As the amount of organic solvent in the buffer increases, hydrophilic peptides begin to elute, followed by more hydrophobic peptides. Thus, by controlling the amount of solvent in the buffer, peptides can be eluted from the mixture one by one into the mass spectrometer. In some implementations, the end of the column may be connected to an electrospray needle that aerosolizes the eluted peptides for presentation into the mass spectrometer.

Steps 520, 530, 540, 550, 560, and 570 are repeated for each peptide type as it elutes from the input mixture. As discussed above, this technique relies upon peptide molecules of a particular peptide being chemically identical (or sufficiently chemically similar that they elute substantially at the same time) and provides one of the two types of multiplexing described herein (the other being that peptides from multiple samples also elute together).

In act 520, an $MS^1$ mass spectrometry stage is performed to measure the mass/charge ratio of the peptides input to the mass spectrometer. The mass/charge ratios of the input peptides may be measured in any suitable way, such as by using a time-of-flight analyzer, a quadrupole mass filter, or an ion trap such as an ORBITRAP®.

In act 530, an isolation window within the mass/charge data is selected for further analysis. The isolation window may be selected based on measurement of the mass/charge of the trigger peptides present and by applying the known offset (e.g., that was supplied with a kit that was used to prepare the input mixture) to identify the isolation window. The mass spectrometer may be programmed to identify the presence of the trigger peptide data based on the known molecular mass of the trigger peptides supplied (e.g., from a kit). The mass spectrometer may then calculate the position and size of the isolation window from data associated with the particular type of peptide associated with the identified trigger peptide. The mass spectrometer may then operate an ion trap or other suitable device to isolate those ions appearing in the isolation window.

In act 540, the contents of the isolation window selected in act 530 are fragmented and measured in the $MS^2$ stage. According to some embodiments, the fragmentation may be performed via collision-induced dissociation (CID), higher-energy collision induced dissociation (HCD), electron transfer dissociation (ETD), or combinations thereof. While the particular technique used to fragment peptides is not critical, there may be an advantage to utilizing HCD when studying phosphorylated peptides. Irrespective of which technique(s) are used to fragment the peptides, the mass/charge ratios of the resulting fragments may be measured in any suitable way, such as by using a time-of-flight analyzer, a quadrupole mass filter, or an ion trap such as an ORBITRAP®.

In act 550, fragments within one or more mass/charge isolation windows are selected for further analysis. Generally, there will be multiple such isolation windows utilized in act 550. The isolation window(s) may be selected based on information about the peptide currently being analyzed, which may be programmed into the mass spectrometer or otherwise available to the mass spectrometer to automatically select the appropriate isolation windows. In act 550, one or more quality assurance filters may also be applied to determine whether to continue analysis of the current peptide, or to return to an earlier step of the analysis (e.g., act 520) based on whether the $MS^2$ data does or does not pass the one or more filters.

In act 560, the contents of the isolation window(s) selected in act 550 are fragmented and measured in the $MS^3$ stage. According to some embodiments, the fragmentation may be performed via collision-induced dissociation (CID). Injection times in act 560 may be selected based on the measure intensity of one or more of the targets identified in act 550.

In act 570, abundances of the peptide currently being analyzed within each sample may be determined. According to some embodiments, a relative abundance for each sample may be determined by comparing the measured abundances of reporter ion fragments and identifying samples corresponding to each reporter ion mass. According to some embodiments, an absolute abundance for each sample may be determined by comparing the measured abundance of reporter ions associated with the quantification peptides with the measured abundances of reporter ion fragments and identifying samples corresponding to each reporter ion mass. Since the amount of the quantification peptides provided in the input mixture is known (e.g., because they were provided in a kit that stated their amount or concentration, and a known amount was added during preparation of the sample mixture), the absolute abundance of the peptide in each sample can be inferred from the measured relative abundances. According to some embodiments, an absolute abundance for each sample may be determined by comparing abundances of the trigger peptides and the peptides in the isolation window measured in acts 520-530. If an amount of the trigger peptides are known (e.g., because they were provided in a kit that stated their amount or concentration, and a known amount was added during preparation of the sample mixture), the absolute abundance of all of the corresponding peptides from the samples can be inferred by comparing the two abundances.

Figure 6:
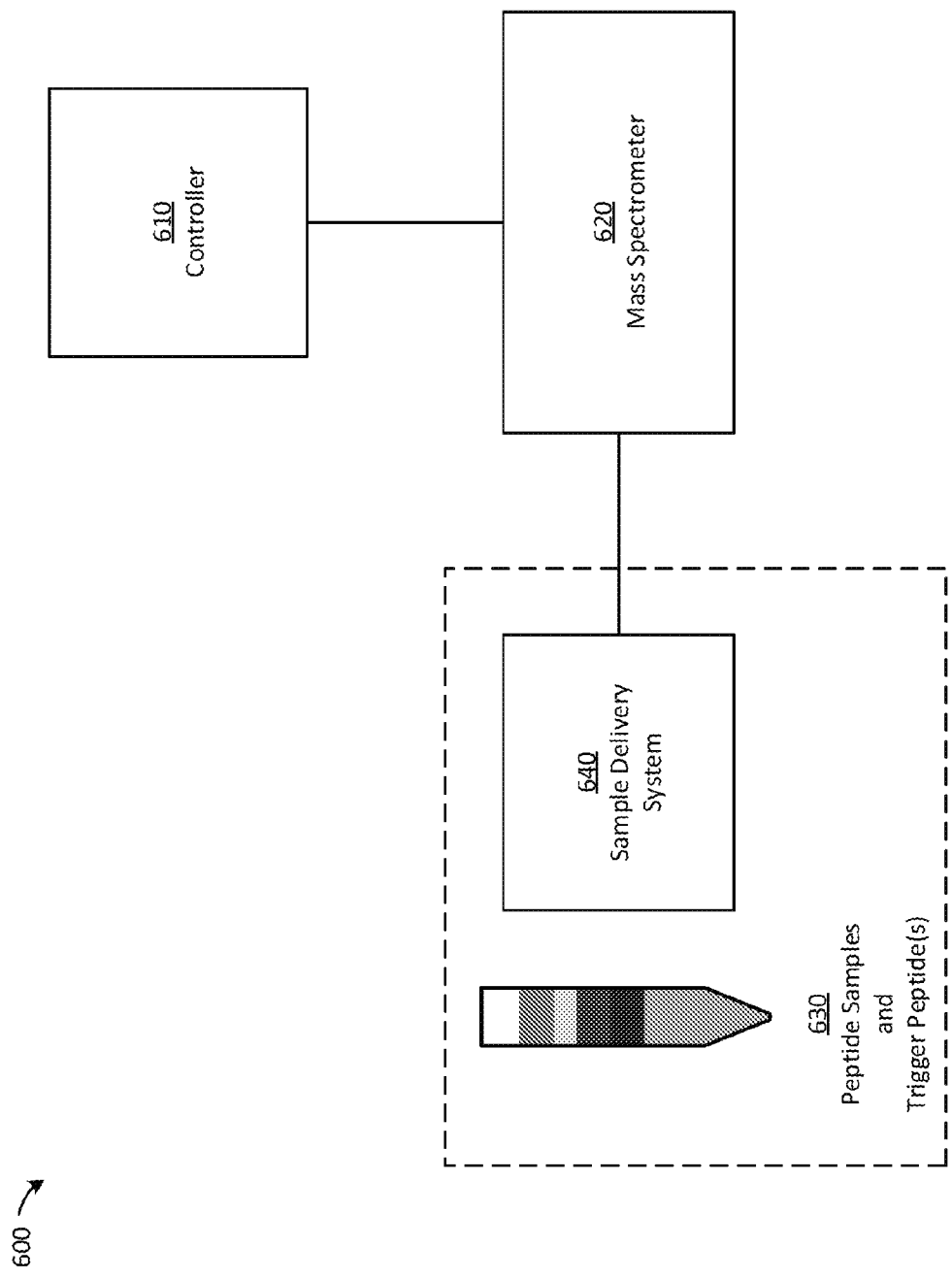
FIG. 6 illustrates a system suitable for controlling a mass spectrometer in accordance with techniques described herein, according to some embodiments.

FIG. 6 illustrates a system suitable for controlling a mass spectrometer in accordance with techniques described herein, according to some embodiments. System 600 includes a controller 610 used to control a mass spectrometer 620, into which peptide samples and trigger peptides 630 are supplied via a sample delivery system.

According to some embodiments, the mass spectrometer may be an ORBITRAP FUSION® TRIBRID®. According to some embodiments, the sample delivery system may include a liquid chromatography system and/or an electrospray. For example, the combination of sample delivery system 640 and mass spectrometer 620 may comprise an LC-MS/MS system.

According to some embodiments, the mass spectrometer may be programmed with, and/or may obtain from controller 610, data used in a proteomic analysis as described herein. Such data may include, but is not limited to: elution order schedules, scaling of $MS^3$ injection times based on intensity of target fragments of interest identified in the $MS^2$ stage, and for a plurality of peptides: $MS^2$ target fragment windows, trigger peptide masses, trigger peptide to isolation window offsets, $MS^1$ isolation window sizes, trigger peptide masses, quantification peptide masses, trigger peptide abundances, quantification peptide abundances, acceptable ranges of ratios of expected fragment abundances, one or more acceptable purity thresholds, or combinations thereof.

Figure 8A:
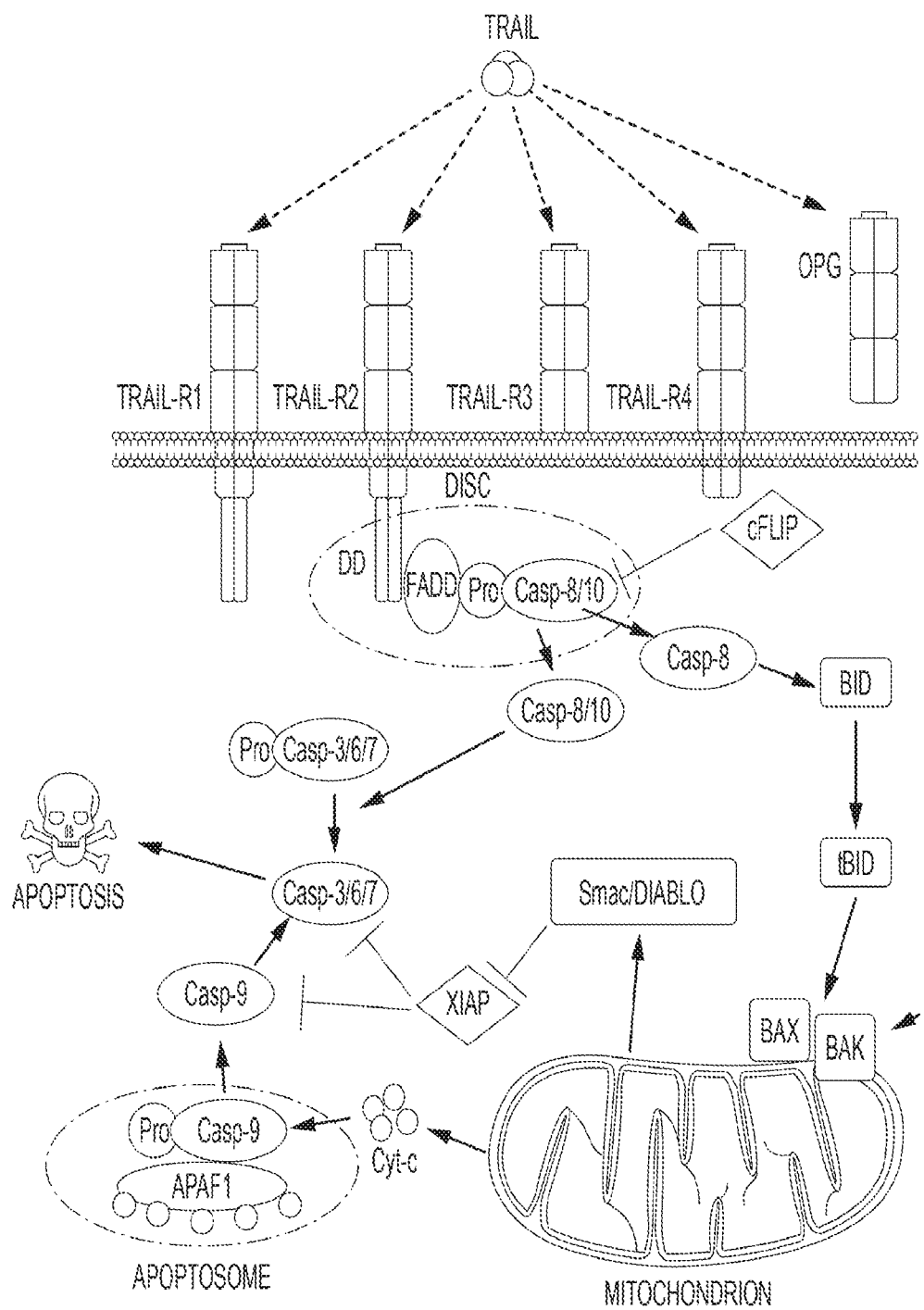
FIGS. 8A-8C illustrate an example of applying proteomic analysis techniques to measure abundances of apoptosis pathway members.

The following describes a non-limiting example of applying above-described techniques to measure abundances of apoptosis pathway members. Apoptosis (programmed cell death) is part of normal cell turnover, and many diseases are characterized by abnormal levels of apoptosis. For instance, levels of apoptosis may be reduced in the case of cancer or elevated in the case of a neurodegenerative disease. The apoptosis pathway is illustrated in FIG. 8A. The absolute levels of apoptotic pathway proteins have been shown to correlate with sensitization to chemical compounds. Accordingly, by measuring absolute and/or relative abundances of apoptosis pathway members (see Table 1 below), these findings may be correlated to drug sensitivity. For instance, the abundances may indicate sensitivity to apoptosis inducing drugs, such as TRAIL, across numerous cell lines including the NCI-60.

As described above, analysis of apoptotic pathway proteins may be performed more quickly and more accurately by making available combinations of mass-tagged peptides as a kit to be mixed with biological samples on which the apoptotic pathway analysis is to be performed. Such a kit can include tagged synthetic peptides with molecular masses offset from masses of sample peptides prepared for analysis. The sample peptides, once prepared for analysis using the kit, can also be mass-tagged so that the tagged synthetic peptides in the kit are chemically identical to the prepared sample peptides. An illustrative kit for performing an apoptosis pathway analysis may thereby include one or more peptides selected from amongst those proteins shown in Table 1. These synthetic peptides may be mass-tagged such that there will be a known molecular mass offset between the synthetic peptides and the mass-tagged peptides of the samples.

TABLE 1

| Gene Name | Protein Name |
|---|---|
| APAF1 | Apoptotic protease-activating factor 1 |
| BAD | Bcl2-associated agonist of cell death |
| BAK1 | Bcl-2 homologous antagonist/killer |
| BAX | Apoptosis regulator BAX |
| BBC3 | Bcl-2-binding component 3 |
| BBC3 | Bcl-2-binding component 3 |
| BCL2 | Apoptosis regulator Bcl-2 |
| BCL2A1 | Bcl-2-related protein A1 |
| BCL2L1 | Bcl-2-like protein 1 |
| BCL2L11 | Bcl-2-like protein 11 |
| BCL2L2 | Bcl-2-like protein 2 |
| BFAR | Bifunctional apoptosis regulator |
| BID | BH3-interacting domain death agonist |
| BIRC2 | Baculoviral IAP repeat-containing protein 2 |
| BIRC3 | Baculoviral IAP repeat-containing protein 3 |
| BIRC5 | Baculoviral IAP repeat-containing protein 5 |
| BNIP3 | BCL2/adenovirus E1B 19 kDa protein-interacting protein 3 |
| BNIP3L | BCL2/adenovirus E1B 19 kDa protein-interacting protein 3-like |
| BOK | Bcl-2-related ovarian killer protein |
| CASP10 | Caspase-10 precursor |

TABLE 1-continued

| Gene Name | Protein Name |
|---|---|
| CASP2 | Caspase-2 precursor |
| CASP3 | Caspase-3 precursor |
| CASP6 | Caspase-6 precursor |
| CASP7 | Caspase-7 precursor |
| CASP8 | Caspase-8 precursor |
| CASP9 | Caspase-9 precursor |
| CDH1 | Cadherin-1 precursor |
| CFLAR | CASP8 and FADD-like apoptosis regulator precursor |
| CHUK | Inhibitor of nuclear factor kappa-B kinase subunit alpha |
| CUL3 | Cullin-3 |
| CYC1 | Cytochrome c1, heme protein, mitochondrial precursor |
| DIABLO | Diablo homolog, mitochondrial precursor |
| FADD | FAS-associated death domain protein |
| HRK | Activator of apoptosis harakiri |
| MCL1 | Induced myeloid leukemia cell differentiation protein Mcl-1 |
| PMAIP1 | Phorbol-12-myristate-13-acetate-induced protein 1 |
| RIPK1 | Receptor-interacting serine/threonine-protein kinase 1 |
| TNFRSF10A | Tumor necrosis factor receptor superfamily member 10A precursor |
| TNFRSF10B | Tumor necrosis factor receptor superfamily member 10B precursor |
| TNFRSF10C | Tumor necrosis factor receptor superfamily member 10C precursor |
| TNFRSF10D | Tumor necrosis factor receptor superfamily member 10D precursor |
| TNFSF10 | Tumor necrosis factor ligand superfamily member 10 |
| TRADD | Tumor necrosis factor receptor type 1-associated DEATH domain protein |
| TRAF2 | TNF receptor-associated factor 2 |
| XIAP | E3 ubiquitin-protein ligase XIAP |

To better understand the pharmacology of apoptosis inducing drugs, an assay was created targeting apoptosis pathway members that was multiplexed in two dimensions: analyte (100 peptides/run) and sample (10 samples/run), using the analysis techniques described above. In this illustrative example, a synthetic version of the peptide (without heavy isotopes), is labeled with a heavy isotope version of the TMT tag weighing 6.01 Da more than the TMT-10 tag. This heavy-TMT labeled peptide is spiked in at high abundance (~200 fmol on column) and upon triggering of this peptide, the MS is directed to quantify offset from this trigger, the natively expressed peptide which is labeled with TMT-10. Absolute quantification is achievable by either the Trigger/Target MS1 ratio, or by spiking in a version of the peptide at much lower abundance (~200 amol) into either the 131n or 131c (TMT-11) channel as an MS3 based absolute reference. While discovery proteomics analysis are typically optimized to exclude z=1 peptides, including them in this targeted assay had no negative impact. A particularly useful case was the C-terminal peptide (K.LILSYT.-) of the apoptosis regulator CFLAR, which is present in some but not all isoforms, allowing isoform specific quantification. Discovery platforms also typically use a single mode of fragmentation, but using the ORBITRAP® LUMOS®, we were able to optimally fragment some peptides with HCD and others with CID during a single assay. During our initial comparison of TRAIL response variants, preliminary findings suggest that the resistance to TRAIL observed in the MCF7 breast cancer cell line, is due in part to a high XIAP/CASP3 ratio, resulting in low CASP3 activity. Future work will expand our cell measurements to include triplicate analysis of the NCI-60 cancer cell library, which has publically available drug response data.

Figure 8B:
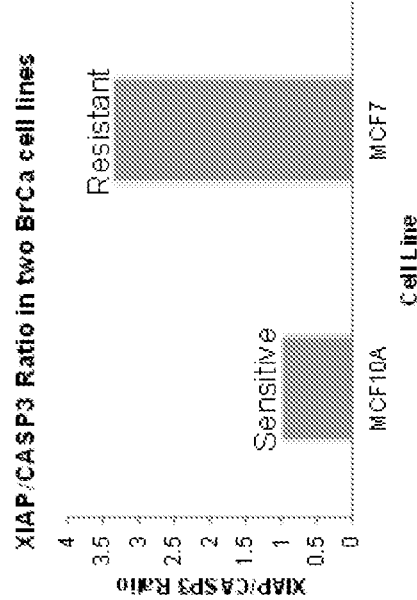
Figure 8C:
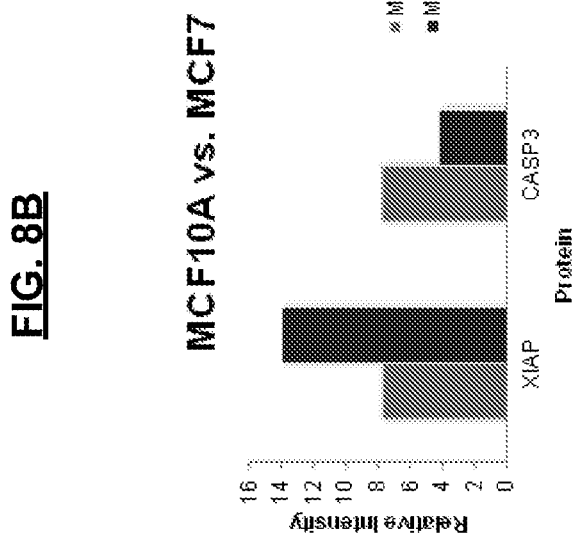

Examining the fold-change of individual proteins may be informative, but in cases where two proteins have opposing functions, the ratio of these proteins may be more informative. As shown in FIGS. 8B and 8C, the observed fold change was nearly double between a TRAIL resistant and a TRAIL sensitive cell line once the ratio of XIAP/CASP3 is determined. CASP3 activity is required for TRAIL-induced apoptosis.

Figure 7:
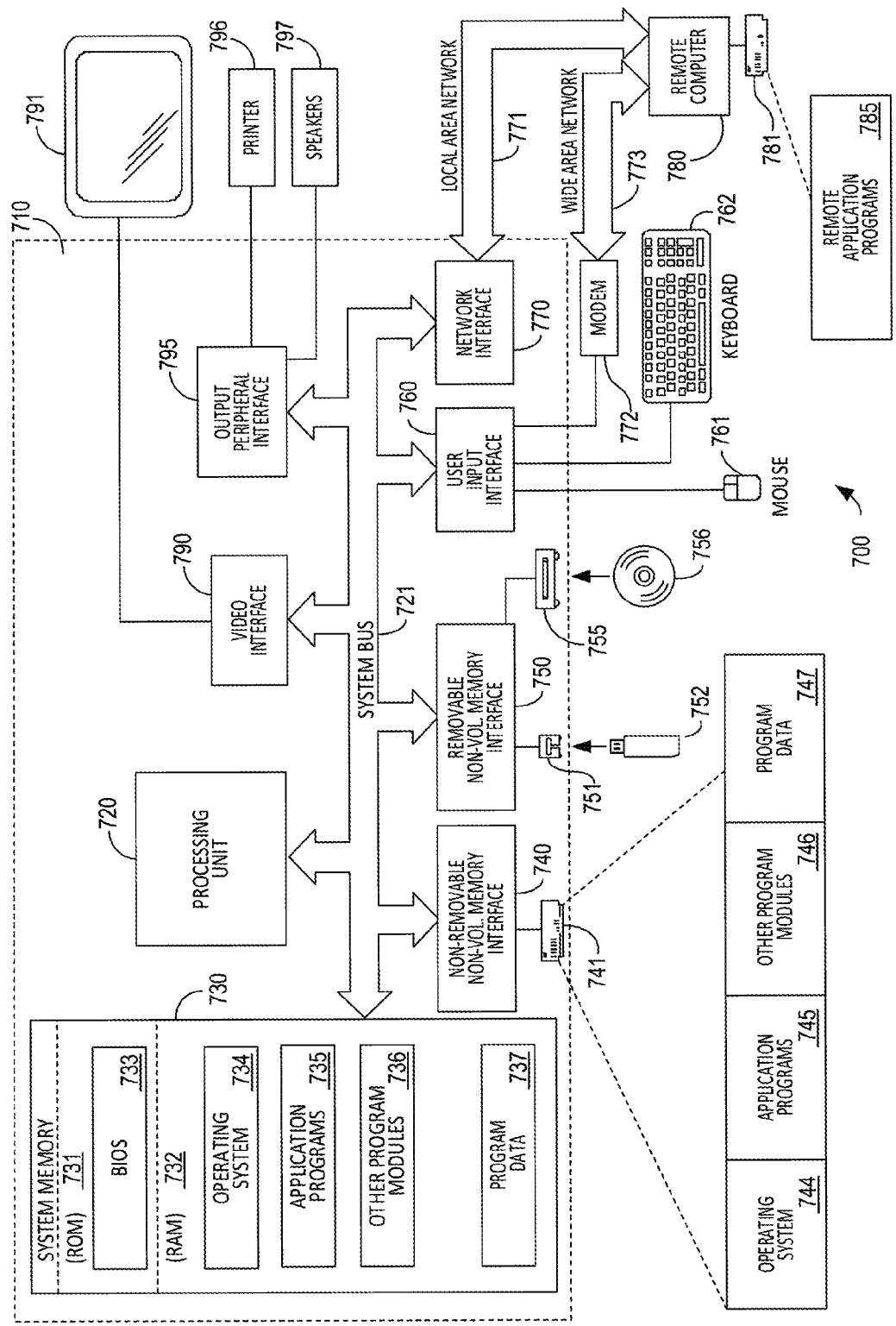
FIG. 7 illustrates an example of a computing system environment on which aspects of the invention may be implemented.

FIG. 7 illustrates an example of a suitable computing system environment 700 on which the technology described herein may be implemented. For example, some or all components of computing system environment 700 may be used to control a mass spectrometer in performing a proteomic analysis as described herein (e.g., may be used as controller 610 in FIG. 6). The computing system environment 700 is only one example of a suitable computing environment and is not intended to suggest any limitation as to the scope of use or functionality of the technology described herein. Neither should the computing environment 700 be interpreted as having any dependency or requirement relating to any one or combination of components illustrated in the illustrative operating environment 700.

The technology described herein is operational with numerous other computing system environments or configurations. Examples of computing systems, environments, and/or configurations that may be suitable for use with the technology described herein include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The technology described herein may also be practiced in distributed computing environments where tasks are performed by remote processing devices that are linked through a communications network. In a distributed computing environment, program modules may be located in both local and remote computer storage media including memory storage devices.

With reference to FIG. 7, an illustrative system for implementing the technology described herein includes a computing device in the form of a computer 710. Components of computer 710 may include, but are not limited to, a processing unit 720, a system memory 730, and a system bus 721 that couples various system components including the system memory to the processing unit 720. The system bus 721 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 710 typically includes a variety of computer readable media. Computer readable media can be any available media that can be accessed by computer 710 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data.

Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 710. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 730 includes computer storage media in the form of volatile and/or nonvolatile memory such as read only memory (ROM) 731 and random access memory (RAM) 732. A basic input/output system 733 (BIOS), containing the basic routines that help to transfer information between elements within computer 710, such as during start-up, is typically stored in ROM 731. RAM 732 typically contains data and/or program modules that are immediately accessible to and/or presently being operated on by processing unit 720. By way of example, and not limitation, FIG. 7 illustrates operating system 734, application programs 735, other program modules 736, and program data 737.

The computer 710 may also include other removable/non-removable, volatile/nonvolatile computer storage media. By way of example only, FIG. 7 illustrates a hard disk drive 741 that reads from or writes to non-removable, nonvolatile magnetic media, a magnetic disk drive 751 that reads from or writes to a removable, nonvolatile storage unit 752 (e.g., a flash memory drive having a Universal Serial Bus (USB) interface or other suitable interface), and an optical disk drive 755 that reads from or writes to a removable, non-volatile optical disk 756 such as a CD ROM or other optical media. Other removable/non-removable, volatile/nonvolatile computer storage media that can be used in the illustrative operating environment include, but are not limited to, magnetic tape cassettes, flash memory cards, digital versatile disks, digital video tape, solid state RAM, solid state ROM, and the like. The hard disk drive 741 is typically connected to the system bus 721 through a non-removable memory interface such as interface 740, and magnetic disk drive 751 and optical disk drive 755 are typically connected to the system bus 721 by a removable memory interface, such as interface 750.

The drives and their associated computer storage media discussed above and illustrated in FIG. 7, provide storage of computer readable instructions, data structures, program modules and other data for the computer 710. In FIG. 7, for example, hard disk drive 741 is illustrated as storing operating system 744, application programs 745, other program modules 746, and program data 747. Note that these components can either be the same as or different from operating system 734, application programs 735, other program modules 736, and program data 737. Operating system 744, application programs 745, other program modules 746, and program data 747 are given different numbers here to illustrate that, at a minimum, they are different copies. A user may enter commands and information into the computer 710 through input devices such as a keyboard 762 and pointing device 761, commonly referred to as a mouse, trackball or touch pad. Other input devices (not shown) may include a microphone, joystick, game pad, satellite dish, scanner, or the like. These and other input devices are often connected to the processing unit 720 through a user input interface 760 that is coupled to the system bus, but may be connected by other interface and bus structures, such as a parallel port, game port or a universal serial bus (USB). A monitor 791 or other type of display device is also connected to the system bus 721 via an interface, such as a video interface 790. In addition to the monitor, computers may also include other peripheral output devices such as speakers 797 and printer 796, which may be connected through an output peripheral interface 795.

The computer 710 may operate in a networked environment using logical connections to one or more remote computers, such as a remote computer 780. The remote computer 780 may be a personal computer, a server, a router, a network PC, a peer device or other common network node, and typically includes many or all of the elements described above relative to the computer 710, although only a memory storage device 781 has been illustrated in FIG. 7. The logical connections depicted in FIG. 7 include a local area network (LAN) 771 and a wide area network (WAN) 773, but may also include other networks. Such networking environments are commonplace in offices, enterprise-wide computer networks, intranets and the Internet.

When used in a LAN networking environment, the computer 710 is connected to the LAN 771 through a network interface or adapter 770. When used in a WAN networking environment, the computer 710 typically includes a modem 772 or other means for establishing communications over the WAN 773, such as the Internet. The modem 772, which may be internal or external, may be connected to the system bus 721 via the user input interface 760, or other appropriate mechanism. In a networked environment, program modules depicted relative to the computer 710, or portions thereof, may be stored in the remote memory storage device. By way of example, and not limitation, FIG. 7 illustrates remote application programs 785 as residing on memory device 781. It will be appreciated that the network connections shown are illustrative and other means of establishing a communications link between the computers may be used.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A kit for performing an assay to determine a disease and/or condition state of an organism, the kit comprising:
   a plurality of peptides proteotypic of a protein whose expression is characteristic of the disease and/or condition state, wherein the plurality of peptides are mass-tagged peptides,
   wherein the plurality of peptides includes a population of a first peptide mass-tagged with a first mass tag, the population of the first peptide comprising:
      a first plurality of molecules of the first peptide mass-tagged with the first mass tag, each molecule of the first plurality of molecules having a first mass, and
      a second plurality of molecules of the first peptide mass-tagged with the first mass tag, each molecule of the second plurality of molecules having a second mass, different from the first mass,
      wherein molecules of the second plurality of molecules are chemically identical to one another and to each molecule of the first plurality of molecules; and
   information indicating:
      the first mass as a mass spectrometry trigger;
      the first mass tag; and
      the second mass.

2. The kit of claim 1, further comprising:
   information indicating a quantity of the first plurality of molecules of the first peptide and a quantity of the second plurality of molecules of the first peptide.

3. The kit of claim 1, further comprising:
   information indicating a plurality of mass spectrometry target fragment masses.

4. The kit of claim 1, wherein the disease and/or condition state is cancer.

5. A composition of mass-tagged peptide molecules having known molecular masses for use as mass spectrometry triggers, the composition comprising:
   a population of first trigger molecules, wherein each first trigger molecule of the population of first trigger molecules includes a peptide portion bonded to a tag portion, the peptide portion being a first peptide and the tag portion being a first mass tag; and
   a population of second trigger molecules, wherein each second trigger molecule of the population of second trigger molecules includes a peptide portion bonded to a tag portion, the peptide portion being a second peptide, different from the first peptide, and the tag portion being the first mass tag.

6. The composition of claim 5, wherein the peptide portion of the first trigger molecules has a length of at least five amino acids and no more than fifty amino acids.

7. The composition of claim 6, wherein the peptide portion of the first trigger molecules has a length of at least ten amino acids and no more than twenty amino acids.

8. The composition of claim 5, wherein the first mass tag is a tandem mass tag.

9. A kit for performing an assay to determine a disease and/or condition state of an organism, comprising:
   the composition of claim 5,
   wherein the disease and/or condition state is characterized by expression of at least a first protein and a second protein,
   wherein the first peptide is proteotypic of the first protein, and
   wherein the second peptide is proteotypic of the second protein.

10. A kit comprising:
    the composition of claim 5; and
    information indicating a quantity of the first trigger molecules and a quantity of the second trigger molecules.

11. A kit comprising:
    the composition of claim 5; and
    information indicating a molecular mass of the first trigger molecules and a molecular mass of the second trigger molecules.

12. A kit comprising:
    the composition of claim 5; and
    information identifying the first mass tag.

13. A composition of mass-tagged peptide molecules having known molecular masses for use as mass spectrometry triggers, the composition comprising:
    a population of trigger molecules, wherein each trigger molecule of the population of trigger molecules includes a peptide portion bonded to a tag portion, the tag portion being a first mass tag that is not isotopically substituted, wherein the peptide portion includes one or more isotopic substitutions, and wherein the trigger molecules of the population of trigger molecules are chemically identical to one another.

14. The composition of claim 13, wherein the peptide portion of the trigger molecules has a length of at least five amino acids and no more than fifty amino acids.

15. The composition of claim 14, wherein the peptide portion of the trigger molecules has a length of at least ten amino acids and no more than twenty amino acids.

16. The composition of claim 13, wherein the first mass tag is a tandem mass tag.

17. A kit comprising:
    the composition of claim 13; and
    information indicating a quantity of the trigger molecules.

18. A kit comprising:
    the composition of claim 13; and information indicating a molecular mass of the trigger molecules.

* * * * *